United States Patent
Tajima et al.

(10) Patent No.: US 6,432,913 B1
(45) Date of Patent: Aug. 13, 2002

(54) POLYPEPTIDE OF PROTEIN P140 AND DNAS ENCODING IT

(75) Inventors: Hisao Tajima; Koichiro Kitagawa; Hiroyuki Ohno, all of Osaka (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/558,340

(22) Filed: Apr. 26, 2000

Related U.S. Application Data

(62) Division of application No. 09/192,435, filed on Jan. 8, 1998, now Pat. No. 6,303,320, which is a division of application No. 08/571,785, filed on Dec. 13, 1995, now Pat. No. 5,804,411, which is a division of application No. 08/348,143, filed on Nov. 23, 1994, now Pat. No. 5,506,205.

(30) Foreign Application Priority Data

Nov. 24, 1993 (JP) ............................................. 5-315806

(51) Int. Cl.⁷ .......................... A01N 61/00; C12N 9/12; C12Q 1/48; G01N 33/53; C07K 14/00

(52) U.S. Cl. ............................... 514/1; 514/2; 435/193; 435/194; 435/15; 435/7.21; 435/7.8; 530/350

(58) Field of Search ........................ 530/350; 435/183, 435/193, 194, 7.21, 7.8, 15; 514/2, 1

(56) References Cited

U.S. PATENT DOCUMENTS

| | | | |
|---|---|---|---|
| 5,506,205 A | 4/1996 | Tajima et al. | 514/12 |
| 5,804,411 A | 9/1998 | Tajima et al. | 435/69.1 |
| 5,817,471 A * | 10/1998 | Kaplan | 435/7.21 |

OTHER PUBLICATIONS

Bohme et al. "EPHRIN Type–B receptor 3 precursor", Database: SwissProt, Accession No. P54753.*

Dekowski et al. "A Tyrosine Kinase associated with the Red Cell Membrane Phosphorylates Band 3", The J. of Biol. Chem., vol. 258, pp 2750–2753, Mar. 10, 1983.*

Database GenBank on STN (1996) Bohme et al. Accession No. P54753.

Bohme et al. (1993) Oncogene 8:2857–62.

* cited by examiner

Primary Examiner—Karen Cochrane Carlson
Assistant Examiner—Rita Mitra
(74) Attorney, Agent, or Firm—Sughrue Mion, PLLC

(57) ABSTRACT

The present invention is related to a novel protein p140 polypeptide which is a key protein involved in the signal transmission system of insulin; method for preparation of it; DNA encoding the said polypeptide; vector derived the said DNA; host cells transformed the said vector; antibody of the said polypeptide; pharmaceutical composition containing the said peptide or antibody; method for the prevention and/or treatment of diabetes, which is characterized by tyrosine phosphorylation of the said protein p140; agent for the prevention and/or treatment for the currently said the prevention and/or treatment method; agent for the prevention and/or treatment of diabetes, which is characterized by containing a compound which can tyrosine phosphorylation of protein p140, as active ingredient and the screening methods of the said prevention and/or treatment agent.

Tyrosine phosphorylation of protein p140 is an essential step in the induction of hypoglycemia by glucose uptake. Method and agent of prevention and/or treatment based on tyrosine phosphorylation of protein p140 in the present invention is not only improve the diabetes-derived hyperglycemic conditions but are also useful for the treatment and/or prevention of diabetes, especially non-insulin dependent diabetes mellitus (NIDDM).

1 Claim, 5 Drawing Sheets

POLYPEPTIDE OF PROTEIN P140 AND DNAS ENCODING IT

This is a divisional of Application No. 09/192,435 filed Jan. 8, 1998 and issued as U.S. Pat. No 6,303,320, which is a divisional of Application No. 08/571,785 filed Dec. 13, 1995 and issued as U.S. Pat. No. 5,804,411, which is a divisional of Application No. 08/348,143 filed Nov. 23, 1994 and issued as U.S. Pat. No. 5,506,205, the disclosures of which are incorporated herein by reference.

SUMMARY

The present invention is related to a novel protein p140 polypeptide which is a key protein involved in the signal transmission system of insulin; method for preparation of it; DNA encoding the said polypeptide; vector derived the said DNA; host cells transformed the said vector; antibody of the said polypeptide; pharmaceutical composition containing the said peptide or antibody; method for the prevention and/or treatment of diabetes, which is characterized by tyrosine phosphorylation of the said protein p140 (to be quoted henceforth as phosphorylation in the present detailed specification); agent for the prevention and/or treatment for the currently said the prevention and/or treatment method; agent for the prevention and/or treatment of diabetes, which is characterized by containing a compound which can tyrosine phosphorylate of protein p140, as active ingredient and the screening methods of the said prevention and/or treatment agent.

BACKGROUND OF INVENTION

Diabetes, an abnormal metabolic disease, is induced by a defect in the mechanism of glucose metabolism.

Under normal conditions, glucose metabolism occurs as follows: Carbohydrates, consumed in the form of food, are digested to glucose in the intestines prior to absorption into the circulatory system. Pancreatic β cells respond to an increase in the blood glucose level by secreting insulin, which in turn stimulates the target peripheral tissues (muscles and liver) to decrease the blood glucose level by enhancing tissue absorption of the blood glucose followed by conversion to glycogen for storage.

Depending on the causative factors, diabetes is classified into two major categories; insulin dependent diabetes mellitus (IDDM) and non-insulin dependent diabetes mellitus (NIDDM). IDDM (Type I diabetes) is a pathological condition where insulin is not secreted or insufficient even on secretion by pancreatic β cells responding to an increase in the blood glucose level induced by food consumption. It has been known that destruction of β cells of the pancreatic islets induces IDDM. The current therapy employs supplementation of insulin from exogenous sources.

NIDDM (Type II diabetes) is a pathological condition where the feedback mechanism of peripheral tissues is dysfunctional and is ineffective in decreasing the blood glucose level although normal insulin secretion occurs within the living system. In the United States of America, NIDDM is said to be a common disease; 5% of the population exceeding 40 years of age suffer from NIDDM. Causative factors involved in this disease have yet to be elucidated.

RELATED ARTS

Elucidation of the etiology of NIDDM; namely, clarification of the insulin-induced glucose uptake mechanism in peripheral tissue cells is, however, unclear as current knowledge on information transmission mechanism of insulin remains limited and unestablished.

Insulin secreted from the pancreatic islets binds with insulin receptors on the cell membrane of peripheral tissue cells. With regards to post-binding information transmission, the phosphorylase cascade and second messenger theories are the current topics of research.

Briefly, these two theories can be accounted as follows:
Phosphorylase Cascade Theory:

When insulin binds with the insulin receptor β subunit, the α subunit existing on the inner cell membrane triggers phosphorylation accompanied by activation of the tyrosine kinase site within the receptor. Phosphorylation of substrates by the latter enzyme produces three different proteins. One is composed of 1,235 amino acids and has a molecular weight of 185 kD corresponding to the insulin receptor substrate-1 (IRS-1). On tyrosine phosphorylation of IRS-1, the phosphorylase for phosphatidylinositol, PI1-kinase, binds against and activates the complex. Post-binding events related to information transmission that concerns localization of glucose transporter within the membrane and membrane ruffling have yet to be established. Other than IRS-1, the existence of two protein substrates (Shc and PTP-1C) has been confirmed. However, the follow-up mechanism(s) has not been completely accounted for.

Second Messenger Theory:

When insulin binds against the insulin receptor, phospholipase C is specifically activated to degrade phosphatidylinositol glycan (PIG) to produce inositolglycan (IG) and diacylglycerol (DAG) by hydrolysis. Although IG has been reported to display various insulin-like effects, the typical glucose uptake effect has yet to be demonstrated.

However, when protein kinase C is activated by DAG, localization of protein kinase C within the cell membrane has been known to be promoted. This implicates that DAG sequentially phosphorylates inner membrane proteins to finally trigger the glucose uptake. However, this implication remains hitherto unclear.

Although the two different schools of thought have hitherto prevailed, initial stages of the post-binding events related to information transmission can only be explained in part by either theory.

According to Copper et al. in 1988 the hormone, amylin, is released from b pancreatic cells that similar to those that secret insulin when hyperglycemia prevails. Based on their findings that amylin inhibited the action of insulin, they revealed that the hormone might be used as an insulin antagonist. A follow-up report in 1991 indicates that the excessive use of amylin in transgenic mice induces NIDDM. However, the relationship of amylin with insulin information transmission remains hitherto unexplored.

MEANS TO SOLVE THE PROBLEMS

The inventors of the present invention focus on the insulin antagonistic properties of amylin. With persistent research activities conducted on the effects of amylin on the insulin information transmission system, the inventors first identified the inhibition site of amylin in regulating the insulin information transmission system and discovered the key proteins, phosphorylated protein 140 and 70 (pp140 and pp70), related to this phenomenon. The present invention reveals clearly the structures of said proteins (DNA base sequences and amino sequences) and elucidation of their functions to totally complement the hitherto deficiently explained insulin information transmission phenomenon.

DISCLOSE OF THE INVENTION

Figure 1:
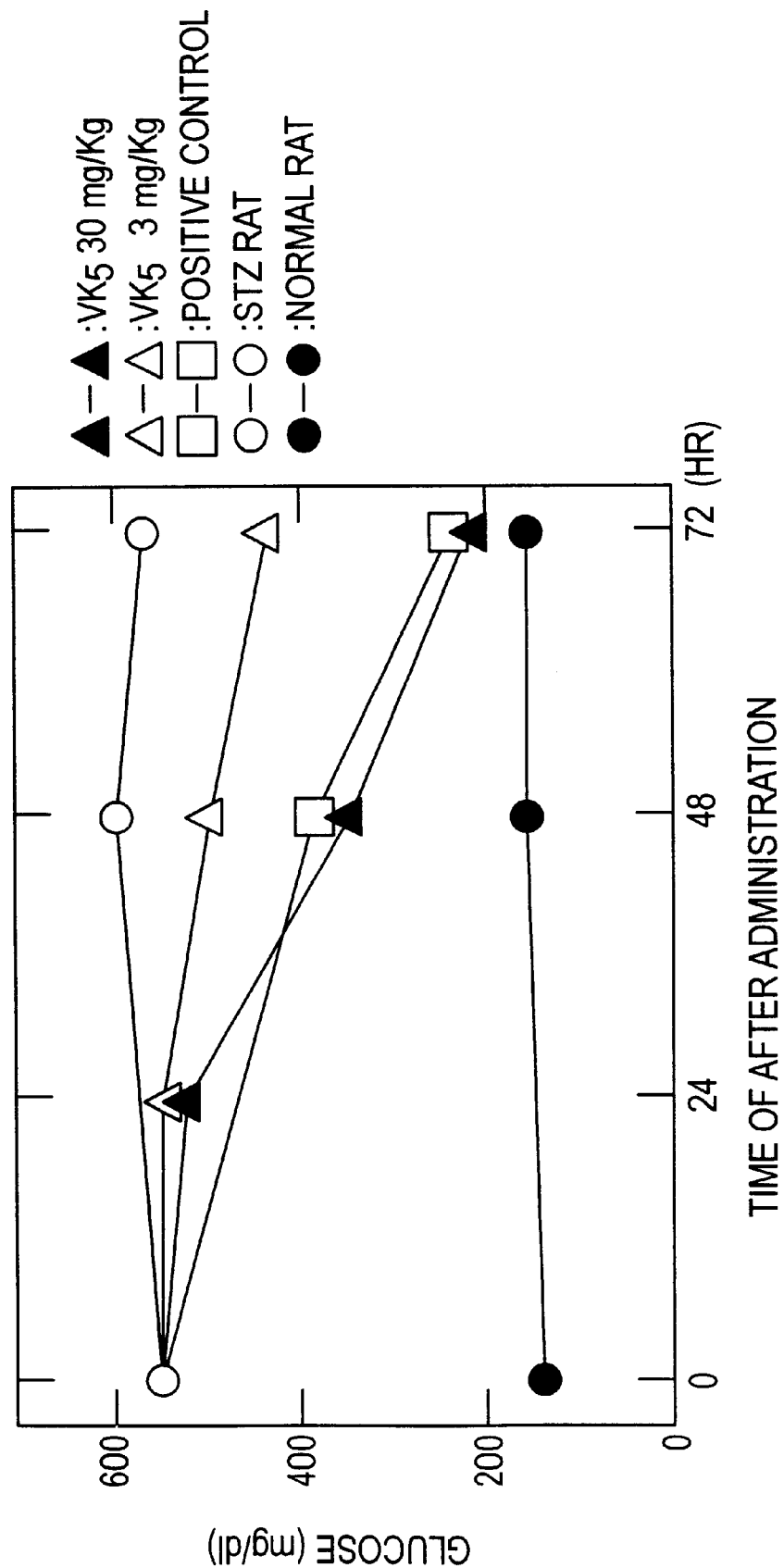
FIG. 1 shows an effects of vitamin $K_5$ ($VK_5$) on blood glucose contents in streptozotocin (STZ)-induced diabetic rats.

The present invention related to homologues and fragment sequences of the genuine amino acid sequence of the said protein p140 constructed from SEQ ID No.1 as shown. In addition, DNAs encoding the related polypeptides of the said homologues and fragment sequences are also encompassed in present invention. Expressed on a more concrete aspect, the said DNAs are those either encoding and/or possessing fragments selectively hybridizing base sequences illustrated in SEQ ID No.2 and 3.

Furthermore, in the present invention, method for the prevention and/or treatment of diabetes, which is characterized by tyrosine phosphorylation of the said protein p140; agent for the prevention and/or treatment for the currently said the prevention and/or treatment method; agent for the prevention and/or treatment of diabetes, which is characterized by containing a compound which can tyrosine phosphorylation of protein p140, as active ingredient and the screening methods of the said prevention and/or treatment agent.

The present invention specifically include:
(1) polypeptides constructed by amino sequence(s) illustrated in SEQ ID No.1.
(2) DNAs encoding polypeptides described in (1).
(3) DNAs possessing base sequences illustrated in SEQ ID No.2.
(4) DNAs possessing base sequences illustrated in SEQ ID No.3.
(5) Method for the prevention and/or treatment of diabetes, which is characterized by tyrosine phosphorylation of protein p140
(6) Agent for the prevention and/or treatment of diabetes, which is characterized by tyrosine phosphorylation of protein p140
(7) Agent for the prevention and/or treatment of diabetes, which is characterized by containing a compound which can tyrosine phosphorylation of protein p140, as active ingredient , and
(8) Method for the screening of the agent for the prevention and/or treatment of diabetes, which is characterized by using protein p140.

On administering amylin (0.1 mg/kg, i.p., t.i.d.) to healthy rats for 7 days, dramatic decreases in both incidences of insulin receptor population and secreted insulin quantity. These observations were accompanied by decreases in both incidences, glucose transporter 4 (Glut 4) quantity and synthesized glycogen content (less than 50% decrease compared to that of control group) with 1.7-fold increase in the blood glucose content. Furthermore, in experiments using L6 cells (ATCC strain No., CRL-1458) of rat skeletal muscle myoblasts, a decreased glucose uptake in the cells was observed with amylin administration.

Next, changes in the insulin-induced tyrosine phosphorylation cascade in skeletal muscle myoblasts treated with amylin were investigated by using the anti-phosphotyrosine antibody with the western blot method. As such, when L6 cells were incubated with insulin in the experiments, tyrosine phosphorylation was enhanced. However, pretreatment with amylin under similar conditions confirmed the presence of two different proteins that inhibited the phosphorylation. These proteins are henceforth termed as pp140 and pp70 according to their respective molecular weights. Furthermore, the precursors of these said proteins prior to phosphorylation are, however, henceforth designated as p140 and p70 respectively.

The inventors prepared, isolated and purified the pp140 and pp70 before determining their partial amino acid sequences. On comparing similarities of the said amino acid sequences with previously documented sequences of polypeptides in Swiss Plot Release 2.0, pp70 coincides with the previous known glucose-regulated protein 70. However, the results postulate pp140 as a totally unknown novel protein. As such, inventors of the present invention isolated mRNA of p140 from the rat skeletal muscle myoblasts and constructed the cDNA using the isolated mRNA of p140 before determining the whole base sequence and complete amino acid sequence of the said protein. The results therefore complement the present invention by revealing successfully a completely novel polypeptide and the total DNA chain encoding this polypeptide.

From the above findings, it is understood that amylin may inhibit phosphorylation of p140 and p70 into pp140 and pp70 respectively. In contrast, when amylin is considered to suppress the process from insulin receptor binding to glucose uptake, it suggests that phosphorylation of p140 and p70 to yield pp140 and pp70 may play an important role in the glucose uptake mechanism of cells.

The inventors of the present invention attempted to elucidate the mechanism(s) of action of p140 and p70 accordingly.

When rat skeletal muscle myoblasts (rat L6 cells) were incubated in insulin-supplemented cultures, incidence of a pp140 band on day 3 with pp140 production on day 9 were persistently observed. At about the similar interval (day 3), incidence of Glut 4 was similarly observed with gradual increases in rat L6 cell division. Furthermore, polynucleation of rat skeletal muscle myoblasts was observed on day 7 in the similar culture system with subsequent division to form the muscle cells. In the case of pp140, the cells appeared on day 7 and persisted to register production of the protein until day 14.

However, on examining localization of pp140 within the cells, the said protein was found within the microsome membrane (MM) of cytoplasm in the cell at post-culture 10 min when insulin was added to non-serum treated L6 cells. The pp140 disappeared thereafter. In addition, pp140 was first observed in the cell permeable membrane (PM) at post-culture 1~hr. From these findings, pp140 is postulated to have synthesized in cell cytoplasm immediately after insulin treatment ensued with transfer of this protein to permeable membrane (PM) 1~2 hr thereafter. Furthermore, when pp70 localization in L6 cells was investigated with a similar experimental approach, pp70 was first located in the MM immediately after initiating the culture, registered a peak phosphorylated quantity at post-culture 10 min and gradually approached non-detectable values at post-culture 3 hr. Moreover, pp70 was also located within the nucleus immediately after initiating the culture, and the protein content gradually increased to register a peak value at post-culture 3 hr. From the above protein localization patterns, pp70 exists in MM in the absence of insulin and this protein is mobilized to the nucleus fraction within 3 hr after insulin treatment.

Based on the above results, pp140 information transmission mechanism may be postulated as follows. In short, when insulin binds to the receptor, the latter is activated by auto-phosphorylation. The information is then subjected to undergo various steps of activation via phosphorylation of protein phosphorylases to subsequently phosphorylate p140 to pp140. The activated pp140 localizes on permeable membrane (PM) surface before p70 is phosphorylated after undergoing various protein phosphorylation processes simultaneously. The phosphorylated pp70 is activated then mobilized to within the nucleus to subsequently trigger biological activities in the Glut 4 expression within the nucleus. Based on this information, Glut 4 produced within the cytoplasm is hence mobilized to localize on the permeable membrane (PM) surface to eventually trigger glucose uptake.

The above information transmission mechanism warrants follow-up experiments to righteously establish concrete evidence of the phenomenon. In any case, it can now be concluded that activation of p140 is an essential step required to induce glucose uptake in cells and subsequent hypoglycemia in the circulatory system.

As such, the present invention is related to method for the prevention and/or treatment of diabetes, especially non-insulin dependent diabetes mellitus (NIDDM), which is characterized by tyrosine phosphorylation of protein p140.

Moreover, the present invention is related to agent for the prevention and/or treatment of diabetes, especially non-insulin dependent diabetes mellitus (NIDDM), which is characterized by tyrosine phosphorylation of protein p140.

In the present invention, method and agent for the prevention and/or treatment of diabetes, which is characterized by tyrosine phosphorylation of protein p140, includes all or whole of the said method and agent for the prevention and/or treatment of diabetes based on the major mechanism of action involving tyrosine phosphorylation of protein p140.

In addition, cells that tyrosine phosphorylate protein p140 are not only confined to skeletal muscle myoblasts (rat L6 cells), but also include all other cells that positively elicits the said phosphorylation. All in all, cells that have been confirmed to display the said phosphorylation include rat FaO hepatocytes, human A673 muscle cells and HepG2 hepatocytes.

Organs other muscles and liver such as the heart, brain, spleen, lungs, kidneys, testes, placenta and pancreas have repeatedly displayed incidences of p140 mRNA of the present invention. Without being confined merely to muscles and liver, the effects of tyrosine phosphorylation may therefore radiate extensively throughout the living system. From this finding, the said mechanism of action of the present invention is hence not limited to muscle and liver cells, but involves the cardiac, encephalic, splenic, pulmonary, renal testical, placental and pancreatic cells as well.

When the polypeptide of the present invention was compared with amino acid sequences of previously known polypeptides recorded with the Swiss Prot Release 2.0, candidates with a complete whole sequence similar to that of the polypeptide was not identified. Furthermore, no a single cDNA of the complete whole polypeptide of the present invention encoding the previously documented nucleotide sequences recorded in the GenBank Release 70 was located. The said peptide of the present invention is hence confirmed to be a completely novel protein.

Additionally, epiterial cell kinase (Eck) and approximately 40% identity were recognized when the results were compared with amino acid sequences of polypeptides previously documented in the Swiss Prot Release 2.0. As such, a novel protein of the present invention was postulated to belong to the Eck family.

In the present invention, a polypeptide of Seq. ID No. 1 in substantially purified form will generally comprise the polypeptide in a production in which more than 90%, e.g. 95%, 98% or 99% of the polypeptide in the production is that of the Seq. ID No. 1.

A polypeptide homologue of the Seq. ID No. 1 will be generally at least 70%, preferably at least 80 or 90% and more preferably at least 95% homologous to the polypeptide of Seq. ID No. 1 over a region of at least 20, preferably at least 30, for instance 40, 60 or 100 more contiguous amino acids. Such polypeptide homologues will be referred to below as a polypeptide according to the invention.

Generally, fragments of Seq. ID No. 1 or its homologues will be at least 10, preferably at least 15, for example 20, 25, 30, 40, 50 or 60 amino acids in length, and are also encompassed by the term "a polypeptide according to the invention" as used herein.

A DNA capable of selectively hybridizing to the DNA of Seq. ID No. 2 or 3 will be generally at least 70%, preferably at least 80 or 90% and more preferably at least 95% homologous to the DNA of Seq. ID No. 2 or 3 over a region of at least 20, preferably at least 30, for instance 40, 60 or 100 or more contiguous nucleotides. Such DNA will be encompassed by the term "DNA according to the invention".

Fragments of the DNA of Seq. ID No. 2 or 3 will be at least 10, preferably at least 15, for example 20, 25, 30 or 40 nucleotides in length, and are also encompassed by the term "DNA according to the invention" as used herein.

A further embodiment of the invention provides replication and expression vectors comprising DNA according to the invention. The vectors may be, for example, plasmid, virus or phage vectors provided with an origin of replication, optionally a promoter for the expression of the said DNA and optionally a regulator of the promoter. The vector may contain one or more selectable marker genes, for example a anpicillin resistance gene. The vector may be used in vitro, for example of the production of RNA corresponding to the DNA, or used to transfect or transform a host cell.

A further embodiment of the invention provides host cells transformed or transfected with the vectors for the replication and expression of DNA according to the invention, including the DNA SEQ. ID No. 2 or 3 or the open reading frame thereof. The cells will be chosen to be compatible with the vector and may for example be bacterial, yeast, insect or mammalian.

A further embodiment of the invention provides a method of producing a polypeptide which comprises culturing host cells of the present invention under conditions effective to express a polypeptide of the invention. Preferably, in addition, such a method is carried out under conditions in which the polypeptide of the invention is expressed and then produced from the host cells.

DNA according to the invention may also be inserted into the vectors described above in an antisense orientation in order to proved for the production of antisense RNA. Antisense RNA may also be produced by synthetic means. Such antisense RNA may be used in a method of controlling the levels of a polypeptide of the invention in a cell.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen.

Polyclonal antibodies may also be prepared by conventional means which comprise inoculating a host animal, for example a rat or a rabbit, with a polypeptide of the invention and recovering immune serum.

The present invention also provides pharmaceutical compositions containing a polypeptide of the invention, or an antibody thereof, in association with a pharmaceutically acceptable diluent and/or carrier.

The polypeptide of the present invention includes that which a part of their amino acid sequence is lacking (e.g., a polypeptide comprised of the only essential sequence for revealing a biological activity in an amino acid sequence shown in SEQ ID No.1), that which a part of their amino acid sequence is replaced by other amino acids (e.g., those replaced by an amino acid having a similar property) and that which other amino acids are added or inserted into a part of their amino acid sequence, as well as those having the amino acid sequence shown in SEQ ID NO. 1.

As known well, there are one to six kinds of codon as that encoding one amino acid (for example, one kind of codon for Met, and six kinds of codon for Leu) are known. Accordingly, the nucleotide sequence of DNA can be changed in order to encode the polypeptide having the same amino acid sequence.

The DNA of the present invention, specified in (2) includes a group of every nucleotide sequences encoding polypeptides (1) shown in SEQ ID NO. 1 . There is a probability of improving a yield of production of a polypeptide by changing a nucleotide sequence.

The DNA specified in (3) is the embodiment of DNA shown in (2), and is sequence in the natural form.

The DNA shown in (4) indicates the sequence of the DNA specified in (3) with a non-translational region.

The DNA having a nucleotide sequence shown in SEQ ID NO. 3 may be prepared according to the following methods, that is:

(i) by isolating mRNA from a cell line which produces the polypeptide of the present invention (e.g., rat skeletal muscle myoblasts L6 cell), (ii) by preparing first strand (single stranded DNA) from mRNA thus obtained, followed by preparing second strand (double stranded DNA) (synthesis of cDNA), (iii) by inserting cDNA thus obtained into a proper plasmid vector, (iv) by transforming host cells with the recombinant DNA thus obtained (preparation of cDNA library), (v) by random-cloning on a large scale from cDNA library thus obtained, followed by sequencing average 300 bases from 5' end of each clone, and (vi) by sequencing complete length of a clone which has a novel base sequence.

Explained in detail, step (i) may be carried out in accordance with the method of Okayama, H. et al. (described in Methods in Enzymology, 154, 3, (1987)) using L6 cells of a rat skeletal muscle myoblasts which is logarithmic growth phase. Examples of the cells which produce the polypeptide of the present invention is rat or human of muscle, liver, heart, brain, spleen, lungs, kidneys, testes, placenta or pancreas, and is preferably rat skeletal muscle myoblasts L6 cell (ATCC strain No., CRL-1458), rat liver FaO cell, human muscle A673 cell or human liver HepG2 cell. Steps (ii), (iii) and (iv) are a series of steps for preparing cDNA library, and may be carried out in accordance with the method of Gubler & Hoffman (Gene, vol. 25, pp. 263, 1983) with a slight modification. As examples of the plasmid vector used in the step (iii), many vectors functioning in an $E.$ $coli$ strain (e.g., pBR 322) and in a Bacillus subtilis (e.g., pUB 110) are known, and pGEM-3Zf(+) (3,199 bp, manufactured by Promega Corp.) which functions in an $E.$ $Coli$, may be preferably used. As examples of host used in the step (iv), many cells are already known. Any cells may be used, and DH5 competent cell which has been prepared in accordance with the method described in Gene, vol. 96, pp. 23, 1990, may be preferably used. The cloning in the step (v) may be carried out by methods known per se and the sequencing may be carried out in accordance with the method of Maxam-Gilbert or the dideoxy termination method. The step (vi).may be carried out in accordance with the method described in Molecular Cloning (written by Sambrook, J., Fritsch, E. F. and Maniatis, T., published by Cold Spring Harbor Laboratory Press in 1989).

As the following step, it is necessary to examine whether or not the DNA thus obtained codes right a produce,protein. The examination requires:

(I) the conversion of the DNA sequence into the amino acid sequence in a possible frame, (II) the confirmation that the DNA thus obtained covers complete or almost complete length of intact mRNA. These confirmation may be carried out after the step (vi) hereinbefore described, and effectively between the step (v) and the step (vi).

The step (II) may be carried out by Northern analysis.

Once the nucleotide sequences shown in SEQ ID NOs. 2 and 3 are determined, DNA of the present invention may be obtained by chemical synthesis, by PCR method or by hybridization making use of a fragment of DNA of the present invention, as a probe. Furthermore, DNA of the present invention may be obtained in a desired amount by transforming with a vector DNA inserted a DNA of the present invention into a proper host, followed by culturing the transformant.

The polypeptides of the present invention (shown in SEQ ID NO. 1) may be prepared by:

(1) isolating and purifying from an organism or a cultured cell, (2) chemically synthesizing, or (3) using a skill of biotechnology, preferably, by the method described in (3).

Examples of expression system when preparing a polypeptide by using a skill of biotechnology is, for example, the expression system of bacteria, yeast, insect cell and mammalian cell.

For example, the expression in $E.$ $coli$ may be carried out by adding the initiation codon (ATG) to 5' end of a DNA encoding a nucleotide sequence shown in SEQ ID NO. 3, connecting the DNA thus obtained to the downstream of a proper promoter (e.g., trp promoter, lac promoter, $\lambda P_L$ promoter, T7 promoter etc.), and then inserting it into a vector (e.g., pBR322, pUC18, pUC19 etc.) which functions in an $E.$ $coli$ strain to prepare an expression vector. Then, an $E.$ $coli$ strain (e.g., $E.$ $coli$ DH1 strain, $E.$ $coli$ JM109 strain, $E.$ $coli$ HB101 strain, etc.) which is transformed with the expression vector thus obtained may be cultured in a proper medium to obtain the desired polypeptide. When a signal peptide of bacteria (e.g., signal peptide of pel B) is utilized, the desired polypeptide may be also secreted in periplasm. Furthermore, a fusion protein with other polypeptide may be also produced easily.

Furthermore, the expression in a mammalian cell may be carried out, for example, by inserting the DNA shown in SEQ ID NO. 3 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.) to obtain an expression vector, and transforming a proper mammalian cell (e.g., monkey COS-7 cell, Chinese hamster CHO cell, mouse L cell etc.) with the expression vector thus obtained, and then culturing the transformant in a proper medium to get a desired polypeptide in the culture medium. The polypeptide thus obtained may be isolated and purified by conventional biochemical methods.

The protein of the present invention includes the reaction products of phosphorylated and/or sugar-chained protein. In short, the present invention contains p140-bound polysaccharide chains and tyrosine phosphorylated p140 (pp140) found in p140 polypeptides.

EFFECTS OF INVENTION

The protein p140 is postulated to possess the above-mentioned mechanism of action. The protein p140 polypeptide of the present invention can therefore not only improve the hyperglycemic conditions when used alone, but can also be useful in prevention and/or treatment for diabetes, especially non-insulin dependent diabetes mellitus (NIDDM).

Further, polyclonal or monoclonal antibody against the protein p140 polypeptide of the present invention can be used in the determination of the amount of the said polypeptide in organism, and thereby, may be utilized for the purpose of investigating the relationship between the said polypeptide and diseases, or for the purpose of diagnosing diseases, and the like. Polyclonal and monoclonal antibody thereof may be prepared by conventional methods by using the said polypeptide or the fragment thereof as an antigen.

The DNA of the present invention may be utilized as an important and essential template in preparing the polypeptide of the present invention which is expected to possess various use or for diagnosis of and in the treatment of gene diseases (the treatment of gene defect disease and the treatment by inhibiting expression of the polypeptide by antisense DNA (RNA), and the like). Further, genomic DNA may be isolated by using the DNA of the present invention as a probe. Similarly, it is possible to isolate genes having high homology to the DNA of the present invention in human or those of other species.

Furthermore, the present invention is related to agent for the prevention and/or treatment of diabetes characterized by containing a compound which can tyrosine phosphorylation of protein p140, as active ingredient.

All in all, tyrosine phosphorylated protein p140 products include not only currently confirmed substances that possess the said activities but also all those substances that will be confirmed to possess the said activities henceforth. At present, it is confirmed that the compounds have activity of tyrosine phosphorylation, for example, (1) the benzene or naphthalene derivatives of the formula (I)

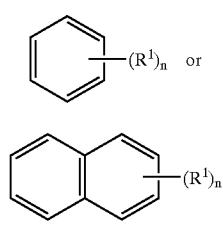

wherein $R^1$ of n species each, independently, is hydrogen atom C1–4 alkyl, hydroxy, amino or $COOR^2$ (in which $R^2$ is hydrogen atom or C1–4 alkyl), n is 1–3 and non-toxic salts thereof and non-toxic acid addition salts thereof, (2) the benzoquinone or naphthoquinone derivatives of the formula (II)

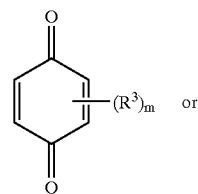

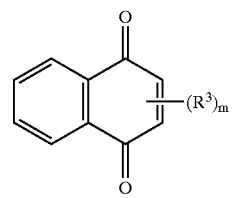

wherein $R^3$ of m species each, independently, is hydrogen atom, C1–12 alkyl, C1–4 alkoxy, C1–4 alkylthio, hydroxy, halogen, phenyl or phenyl substituted by halogen, m is 1–4, (3) the rhodanine or thazolidine derivatives of the formula (III)

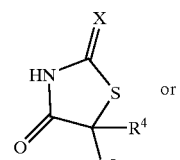

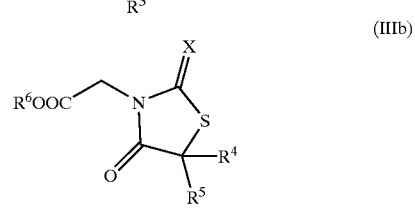

wherein X is oxygen or sulfur atom, $R^4$ and $R^5$ each, independently, is hydrogen atom, phenyl or phenyl substituted by C1–4 alkyl, C1–8 alkoxy, halogen atom or nitro, or $R^4$ and $R^5$, taken together, represent benzylidene, benzylidene substituted by C1–4 alkyl, C1–8 alkoxy, halogen atom or nitro or β-methylcinnamilidene, $R^6$ is hydrogen atom C1–4 alkyl, and non-toxic salts thereof and non-toxic acid-addition salts thereof.

More concretely, the compounds of the formula (I) include 4-amino-2-hydroxybenzoic acid, 4-amino-i-naphthol, 4-amino-2-naphthol, 1-aminonaphthalene, 1,4-dihydroxynaphthalene, 4-amino-2-methyl-1-naphthol (abbreviated as vitamin $K_5$ hereinafter), 1,4-dihydroxy-2-naphthenic acid, etc.

The compounds of the formula (II) include 2-methyl-1,4-benzoquinone, 2,6-di-tert-butyl-1,4-benzoquinone, 2,6-dibromo-1,4-benzoquinone, 2,3,4,5-tetrafluoro-1,4-benzoquinone, 1,4-naphthoquinone, 2-methyl-1,4-naphthoquinone (abbreviated as vitamin K3 hereinafter), 2-hydroxy-3-methyl-1,4-naphthoquinone, 2-(3,7-dimethyloctyl)-3-hydroxy-1,4-naphthoqunone, 2-methoxy-3-methyl-1,4-naphthoquinone, 2-hydroxy-1,4-naphthoquinone, 3-(4-chlorophenyl)-2-hydroxy-1,4-naphthoquinone, 2-propylthio-1,4-naphthoquinone, etc.

The compounds of the formula (III) include 5-phenylrhodanine, 5-phenyl-1,3-thiazodidine-2,4-dione, 5-benzylidenerhodanine, 5-benzylidene-1,3-thiazodidine-2,4-dione, 5,5-diphenylrhodanine, 5,5-diphenyl-1,3-thiazodidine-2,4-dione, 5-(4-isoamyloxybenzylidene) rhodanine, 5-(4-isoamyloxybenzylidene)-1,3-thiazodidine-2,4-diene, 5-(β-methylcinnamylidene)rhodanine-3-acetic acid, etc., and non-toxic salts thereof and non-toxic acid addition salts thereof.

In the present invention, the appropriate non-toxic salts, for example, are salts of alkali metal (e.g., potassium, sodium etc.), salts of alkaline earth metal (e.g., calcium, magnesium etc.), ammonium salts, salts of pharmaceutically-acceptable organic amine (e.g., tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

In the present invention, the appropriate acid addition salts include the salts with inorganic acids such as hydrochloric acid, hydrobromic acid, sulfuric acid, phosphoric acid and nitric acid, and the salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

The compound of the formulae (I), (II) and (III) are well known per se, or used as other starting materials are may be easily prepared by methods known per se.

As the substances used in the present invention are subjected to tyrosine phosphorylation, these agents not only improve the diabetes-derived hyperglycemic conditions but are also useful for the treatment and/or prevention of diabetes, especially non-insulin dependent diabetes mellitus (NIDDM).

It was confirmed that the toxicity of the various active ingredient and salts thereof of the present invention is very low. Therefore, it may be considered that the various active ingredient and acid-addition salts thereof of the present invention are safe and suitable for pharmaceutical use.

For the purpose above described, the polypeptide, each active ingredient and acid addition salts thereof of the present invention, may be normally administered systemically or partially, usually by oral or parenteral administration.

The doses to be administered are determined depending upon e.g., age, body weight, symptom, the desired therapeutic effect, the route of administration, and the duration of the treatment. In the human adult, the doses per person per dose are generally between 10 μg and 1000 mg, by oral administration, up to several times per day, and between 10 μg and 100 mg, by parenteral administration up to several times per day, or by continuous intravenous administration between 1 and 24 hrs. per day.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents (such as lactose), and agents to assist dissolution (such as glutamic acid, asparaginic acid).

The tablets or pills may, if desired, be coated with a film of gastric or enteric material (such as sugar, gelatin, hydroxypropyl cellulose or hydroxypropylmethyl cellulose phthalate), or be coated with more than two films. Coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (such as purified water, ethanol). Besides inert diluents, such compositions may also comprise adjuvants (such as wetting agents, suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate, citric acid). For preparation of such spray compositions, for example, the method described in the U.S. Pat. No. 2,868,691 or 3,095,355 may be used.

Injections for parenteral administration include sterile aqueous or non-aqueous solutions, suspensions and emulsions. In such compositions, one more active compound(s) is or are admixed with at least one inert aqueous diluent(s) (such as distilled water for injection, physiological salt solution) or inert non-aqueous diluent(s) (such as propylene glycol, polyethylene glycol, olive oil, ethanol, POLYSORBATE 80 (registered trade mark)).

Injections may comprise additional materials other than inert diluents: e.g. preserving agents, wetting agents, emulsifying agents, dispersing agents, stabilizing agent (such as lactose), and agents to assist dissolution (such as glutamic acid, asparaginic acid).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by methods known per se.

EXAMPLE

The following examples are illustrated, but not limit, the present invention.

Example 1

Purification Method of pp140

By employing cell trays (225 cm$^2$), rat L6 cells were incubated at 37° C. for 7~10 days in 5% $CO_2$ atmosphere.

Culture media were replaced at 3-day intervals with the Dulbecco's modified Eagle's medium (containing 10% bovine fetal serum (BFS)). Two hours after treating the muscle cells developed from skeletal muscle myoblasts with serum-free medium, 500 μM vanadic acid (vanadate) was added to the culture and allowed to incubate further for 10 min. Cells were then suspended in Tris buffer (400 μM vanadate with protease inhibitor), lysed and centrifuged prior to isolating the supernatant.

The supernatant was adjusted with octa (ethylene glycol) ether ($C_{12}E_8$) to a final concentration of 0.1% before filtration through a millipore membrane. Protein G sepharose gel bound with anti-phosphotyrosine antibodies was filled with the filtered sample. The tyrosine phosphorylated protein (pp140) adsorbed to the gel. After rinsing the column with 25 mM Tris buffer, pp140 was eluted with 10 mM phenylphosphate. The eluate was concentrated with Centricon 30 prior to precipitating pp140 by the acetone precipitation method.

Example 2

Tyrosine Phosphorylation of p140 in Various Tissues

Using the Dubecco's modified Eagle's medium (containing 10% BFS), various cells ($1 \times 10_5$ cells/dish) were incubated at 37° C. under 5% $CO_2$ atmosphere for 5~8 days. The cells were skeletal muscle cells differentiated from skeletal muscle myoblasts. The differentiated cells previously treated in serum-free Dulbecco's modified Eagle's medium for 4 hr was incubated with and without amylin (100 pM) before further incubation for 24 hr. Cultures treated with insulin (100 nM) thereafter were incubated for a fixed interval (10 or 60 min).

After the cultures were rinsed with ice-cold phosphate buffer, cells were lysed with phosphate buffer containing 0.5% octa (ethylene glycol) ether ($C_{12}E_8$). The pp140 was recovered by sepharobeads bound with phosphothyrosine antibody (Transformation Corp.) prior to elution and detection with phenyl phosphate and western blotting method, respectively. The band content of pp140 was determined by a densitometer using purified pp140 as the standard. The results are illustrated in Table 1.

TABLE 1

Effects of p140 tyrosine phosphorylation on various tissues

|  | rat | | human | |
| --- | --- | --- | --- | --- |
|  | L6 | FaO | A 678 | HepG2 |
| control | 300 | 100 | 300 | 250 |
| insulin 10 min | 2400 | 2000 | 2500 | 2100 |
| insulin 60 min | 1000 | 1400 | 1900 | 1200 |
| insulin added amylin 10 min | 180 | 300 | 350 | 300 |
| insulin added amylin 60 min | 200 | 100 | 1000 | 300 |

In the Table 1, cultures were treated with amylin (100 pM) 24 hr before insulin (100 nM) was added.

OBSERVATION

Incidence of pp140, observed when rat L6 cells were incubated with insulin within 10 min, was antagonized by amylin treatment. Moreover, this phenomenon was similarly confirmed in rat hepatocytes, FaO cells. Furthermore, this phenomenon is not merely confined to rats. In human muscle cells (A673 cells) and hepatocytes (HepG2 cells), the phenomenon has been similarly confirmed. It is postulated that amylin suppresses a certain stage or processes before p140 phosphorylation is triggered by the phosphorylation signal of insulin.

Example 3

Effects of Various Test Compounds on p140 Phosphorylation

Rat L6 cells ($1 \times 10^5$ cells/dish) were incubated in the Dulbecco's modified Eagle's medium (containing 10% BFS) at 37° C. under 5% $CO_2$ atmosphere for 8 days. The cells used were skeletal muscle myoblast-differentiated muscle cells. After treating the differentiated skeletal muscle cells in serum-free Dulbecco's modified Eagle's media for 4 hr, various test compounds (10 mM; except insulin,1 mM) were added before the cultures were further incubated for a fixed interval.

After the cultures were rinsed with ice-cold phosphate buffer, cells were lysed with phosphate buffer containing 0.5% octa (ethylene glycol) ether ($C_{12}E_8$). The pp140 was recovered by cephalobeads bound with phosphotyrosine antibody (Transformation Corp.) prior to elution and detection with phenyl phosphate and western blotting method, respectively. The band content of pp140 was determined by a densitometer using purified pp140 as the standard. The results are illustrated in Table 2.

TABLE 2

Effects of p140 tyrosine phosphorylation on various test compounds

| | Amount of tyrosine phosphorylated p140 (copy/cell) | | | |
| --- | --- | --- | --- | --- |
| Compound | 0 | 3 | 10 | 60 (min) |
| Vitamin $K_3$ | 350 | 3650 | 1800 | 750 |
| Vitamin $K_5$ | 400 | 3850 | 2850 | 1600 |
| 5-phenylrhodanine | 350 | 1600 | 1250 | 650 |
| 5-benzylidenerhodanine | 400 | 2650 | 1900 | 1350 |
| 5-(4-isoamyloxybenzylidene) rhodanine | 400 | 3200 | 2250 | 1600 |
| Insulin (positive control) | 350 | 1850 | 2600 | 1650 |

Example 4

Enhancement Activity on Glucose Uptake

Rat L6 cells ($1 \times 10^5$ cells/dish) were incubated in Dulbecco's modified Eagle's medium (containing 10% BFS) at 37° C. under 5% $CO_2$ atmosphere for 8 days. The cells used were skeletal muscle myoblast-differentiated skeletal muscle cells. After treating the differentiated skeletal muscle cells in serum-free Dulbecco's modified Eagle's medium for 2 hr, various test compounds (10 mM; except insulin,1 mM) were added before the cultures were further incubated for a fixed interval of 2 hr. Cultures thereafter treated with Crebs-Ringer phosphate buffer (pH: 7.4) for 20 min were further incubated with 5 mM $^3$H-2-deoxyglucose (0.05 mCi/ml). At the initial 3 min after incubation, the uptake radioactivity content in cells was determined with a liquid syntillation counter. The results are illustrated in Table 3.

TABLE 3

Enhancement activity on glucose uptake

| Compound | Activity on glucose uptake (pmol/mg protein/min) |
|---|---|
| Control | 22.6 |
| Vitamin $K_3$ | 60.9 |
| Vitamin $K_5$ | 67.5 |
| 5-phenylrhodanine | 76.8 |
| 5-benzylidenerhodanine | 84.2 |
| 5-(4-isoamyloxybenzylidene) rhodanine | 98.4 |
| Insulin (positive control) | 106.8 |

Observation

All compounds that promoted p140 phosphorylation were confirmed to activate glucose uptake activities (Table 2 and 3).

Example 5

Effects of Vitamin $K_5$ on Diabetes

Figure 2:
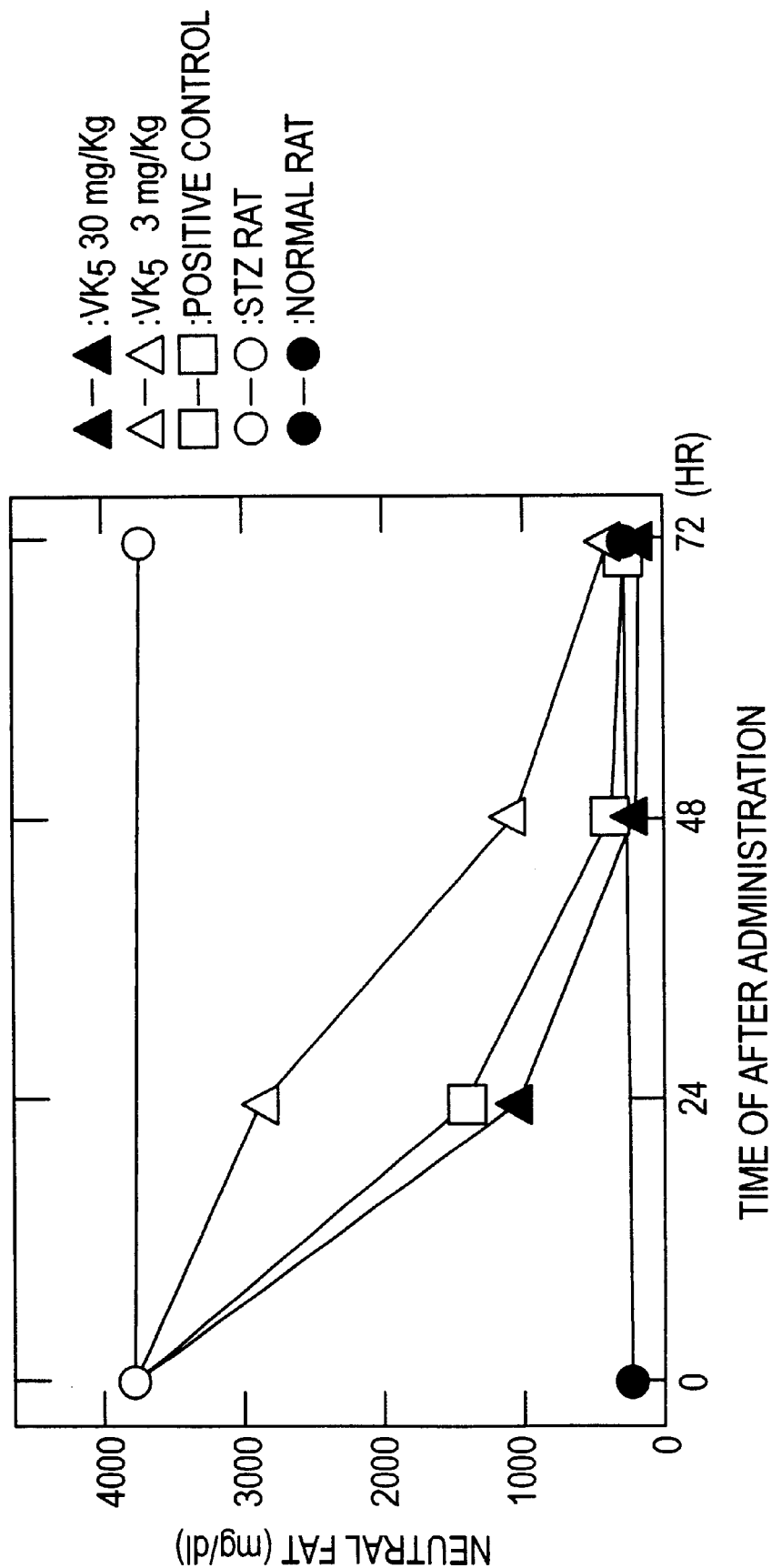
FIG. 2 shows an effects of vitamin $K_5$ ($VK_5$) on neutral fat contents in blood of streptozotocin (STZ)-induced diabetic rats
Figure 3:
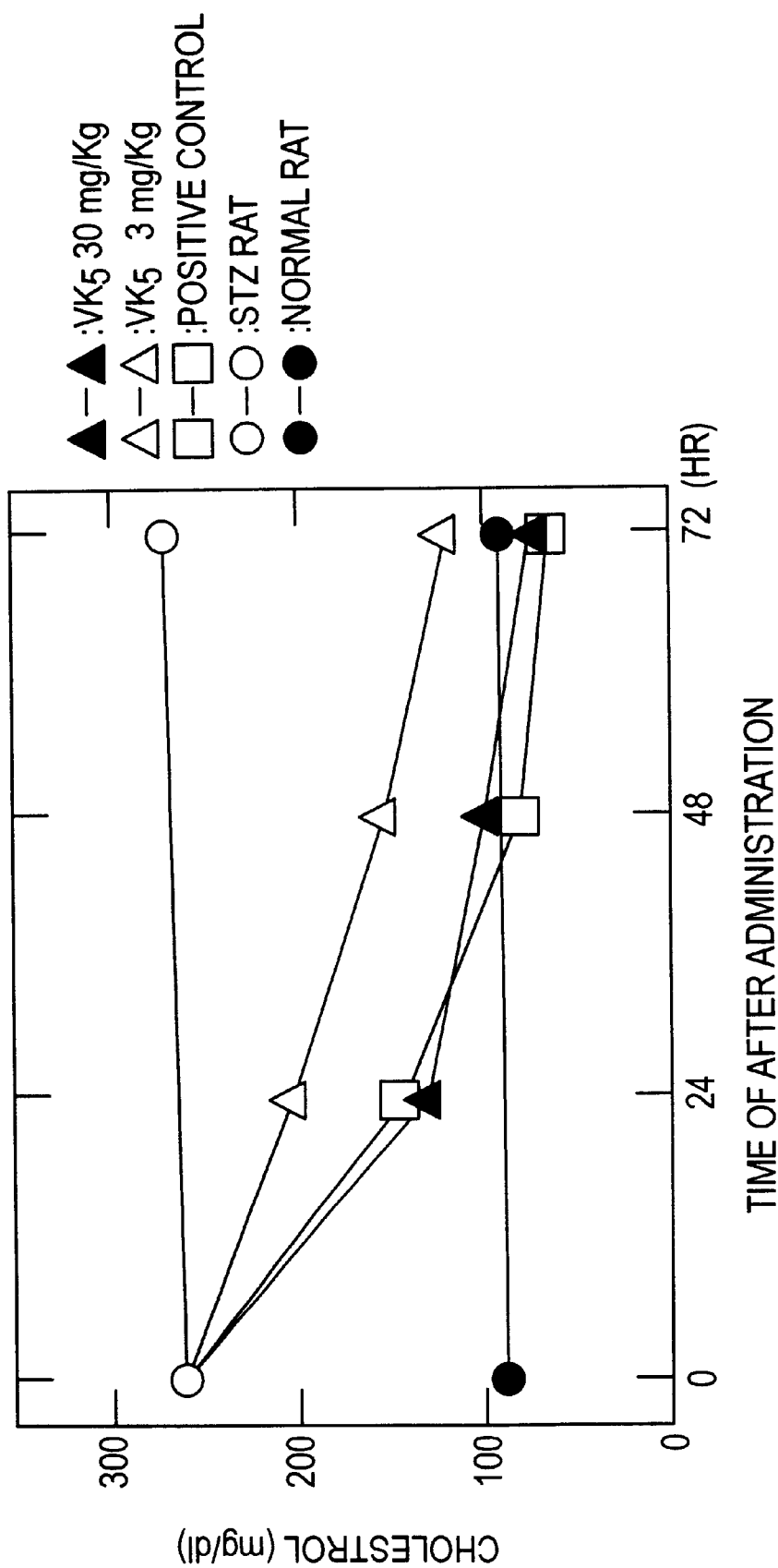
FIG. 3 shows an effects of vitamin $K_5$ ($VK_5$) on blood cholesterol contents in streptozotocin (STZ)-induced diabetic rats

The diabetes model using streptozotocin (STZ) was established in male Wistar rats (STZ rats). After administering various intraperitoneal (i.p.) daily doses of vitamin $K_5$ for 3 consecutive days in STZ rats (one administration per day), the glucose, neutral fat and cholesterol contents in blood were determined. Accordingly, STZ and normal rats were administered with the vehicle (physiological saline) at identical daily rate and duration prior to determination of similar hematic indices mentioned above. In addition, rats administered subcutaneously (s.c.) with insulin (8 U/kg) daily (one administration per day) for 3 consecutive days were used as positive controls. The results are shown in FIG. 1 to 3.

Observations

Administration with vitamin $K_5$ for 3 consecutive days elicited recovery of changes found in all hematic indices in rats; namely, the glucose, neutral fat and cholesterol contents.

Example 6

Analysis of Partial Amino Acid Sequence of pp140 pp140 purified in Example 1 was isolated by electrophoresis, followed by transcription in PVDF membrane, treatmented with trypsin and further isolated with liquid chromatography. The thus isolated pp140 fragment was then sequenced by using the 470A-model automated gas-phase protein sequences/120A-model PTH analyzer (ABI or Applied Biosystem Inc. Corp., U.S.A.) and the extensively employed Edman degradation method prior to determination of its partial amino acid sequence. The sequence is depicted in Sequence Table 5 to 7.

Example 7

Partial Amino Acid Sequencing of pp140 by the Polymerase Chain Reaction (PCR) Method By using extensively applied methods, various primers were derived from the thus isolated partial amino acid fragments, and their respective combinations were conducted before the PCR method was employed. The results revealed a specifically amplified fragment with an approximate length of 400 bp.

Example 8

Isolation and Purification of mRNA

During the log growth phase, mRNA was isolated from $3 \times 10^7$ muscle myoblast L6 cells (ATCC strain No., CRL-1458) according to the method of Okayama et al (Methods in Enzymology, 154, 3 (1987)).

Briefly, after cells were lysed with 5.5 M GTC solution (5.5 M guanidine thiocyanate, 25 mM sodium citrate and 0.5% sodium lauryl sarcosine, the lysate was layered on cesium trifluoroacetate solution (density:1.51) cells lysate and centrifuged at 120,000×g for 20 hr before all the RNA in the pellet was recovered. The RNA sample was passaged through an oligo-dT-cellulose column twice prior to recovery by purification of 106 µg poly(A)+RNA.

Example 9

Tissue Distribution of p140 mRNA

From various tissues, poly(A)+RNA was purified according to procedures similar to those of Example 8. The respective tissue-derived poly(A)+RNA samples (each sample: 2 µg) were subjected to agarose-gel electrophoresis and subsequently transferred through a filter. The 2-kb open reading frame was labeled and used as the internal control before allowed to undergo normal hybridization. Autoradiography was conducted on the specifically bound probe and evaluated by densitometric analyses with an imaging analyzer. When the incidence of β-actin mRNA was taken 100 in the various tissues, relative contents of p140 in tissues are indicated in Table 4.

TABLE 4

Tissue distribution of p140 mRNA

|  | rat | human |
|---|---|---|
| heart | 100 | 100 |
| brain | 240 | 60 |
| spleen | 70 | — |
| lungs | 210 | 100 |
| liver | 130 | 100 |
| muscles | 40 | 130 |
| kidneys | 130 | 40 |
| testes, | 320 | — |
| placenta | — | 220 |
| pancreas | — | 330 |

(—): represents experiments that were not done

Observation

Examination of all the various tissues studied reveals incidences of mRNA, whose effects are though to radiate over an extensive range of tissues. High incidence of mRNA is found especially in the human pancreas.

Example 10

Establishing the cDNA Library

A cDNA library was established according to the modified Gubler and Hoffman method (Gene 25, 263, (1983)).

From poly(A)+RNA (5 µg) derived in Example 2, a first strand was constructed with the reverse transcription enzyme, followed by transformation of a second strand with EcoRI adaptor ligation before excess adaptors and primers were eliminated by gel filtration column chromatography (Sephacryl S-500HR column; Pharmacia Corp.). The remaining 1,620 ng of CDNA fraction was subsequently recovered.

The above construction procedures for cDNA library were accomplished with a λgt 10 cloning system kit (Amersham Corp.).

Next, the λgt 10 phage (Amersham Corp.) and λZAPII phage (Stra Tagene Corp.) were ligated at the EcoRI-treated arms of 1.8-kb mean length. A phage cDNA library of an independent count of $3 \times 10_5$ was established.

Example 11

Cloning and Sequencing

Based on the phage DNA library established in Example 10, clones were duplicated to approximately $1 \times 10_5$ plaques/plate. The approximately 400-bp fragments harvested in Example 7 were designated as probes before screening was conducted. Of the positive controls, subcloning of long strands of the inserts in EcoRI side of plasmid vector pGEM-3Zf(+) (3199 bp; Promega Corp.) was established. T7 or SP6 was sequenced as the primer.

DNA sequencing based on the dideoxy terminator method was performed according to the cyclo-sequencing method using fluorescent di-terminator (ABI, USA). Furthermore, sequence reading was realized with a DNA sequencer (Model 373A; ABI, USA).

As such, nucleotide sequences of mean 300 bases were established from 5' or 3' side of the respective clone.

Example 12

Partial Sequence Analysis

When the nucleotide sequence from Example 11 was subjected to a homology search with all the nucleotide sequences stored in previously registered data base (GenBank and EMBL) with the FASTA program of Lipman and Pearson, the sequenced clones would identify clones containing novel sequences. Nucleotide sequences of the identified clone were converted to amino acid sequences based on 3 possibly constructed frames.

Additionally, novel amino acid sequences in the amino acid sequences were also revealed.

However, the DNA clone that has cloned does not necessarily cover the whole mRNA length. In such a case, the clone is most unlikely to contain the N terminal of amino acid sequence.

As such, the Northern analysis was used to determine if the whole length of the established clone was complemented. In other words, the poly(A)+RNA, isolated from Example 8→Example 9 procedures by electrophoresis, was blotted on a nylon membrane. When the subcloned cDNA insert was hybridized as a probe, a single band at approximately 4400-bp position was observed. Since sizes of the clones were approximated to 2200 bp, PCR was performed at the 5' and 3' sides to read the whole cDNA length with the 3'-RACE (BRL Corp.) system and 5'-RACE (CLONTECH Corp.) system kits.

Example 13

Determining the Sequence and Open Reading Frame of Whole cDNA Length

Random sequencing of the whole length of cDNA sequence was appropriated according to the method of Sambrook et al. (Molecular Cloning: ed. Sambrook J, Fritsch EF, Maniatis T; 1989, Cold Spring Harbor Laboratory Press).

Briefly, plasmid was recovered from the clone and the isolated cDNA insert was then purified before ligation and fragmentation. The terminal of DNA fragment was further smoothened by T4 polymerase and DNA fragments of approximated 400-bp length were recovered by agarose electrophoresis. DNA fragments thus established were subjected to cloning in the SmaI side of plasmid vector and pGEM-3Zf(+) (3199 bp; Promega Corp.) before transformation in E. Coli. Eighty colonies were picked up at random and plasmid DNAs were refined prior to DNA sequencing of these 20 plasmids (possessing cDNA fragments as inserts). DNA sequencing and sequence reading were performed according to the method described in Example 11. Sequence data of cDNA fragments were constructed to the linkage sequences with the DNA sequence program of DNASIS. The basic sequence portaryed in Seq. ID No. 3 was hence constructed. From sequence data of the whole cDNA length, the open reading frame (ORF) was determined. The amino acid sequence was further translated and the sequence thus established is illustrated in Seq. No. 1. One of the frames possesses the 2993-bp ORF, that was approximated to 3,000 bp of the whole ORF length of the Eck family. Therefore, the said polypeptide in the present invention is postulated to possess a whole length of 2,993 bp.

Figure 4:
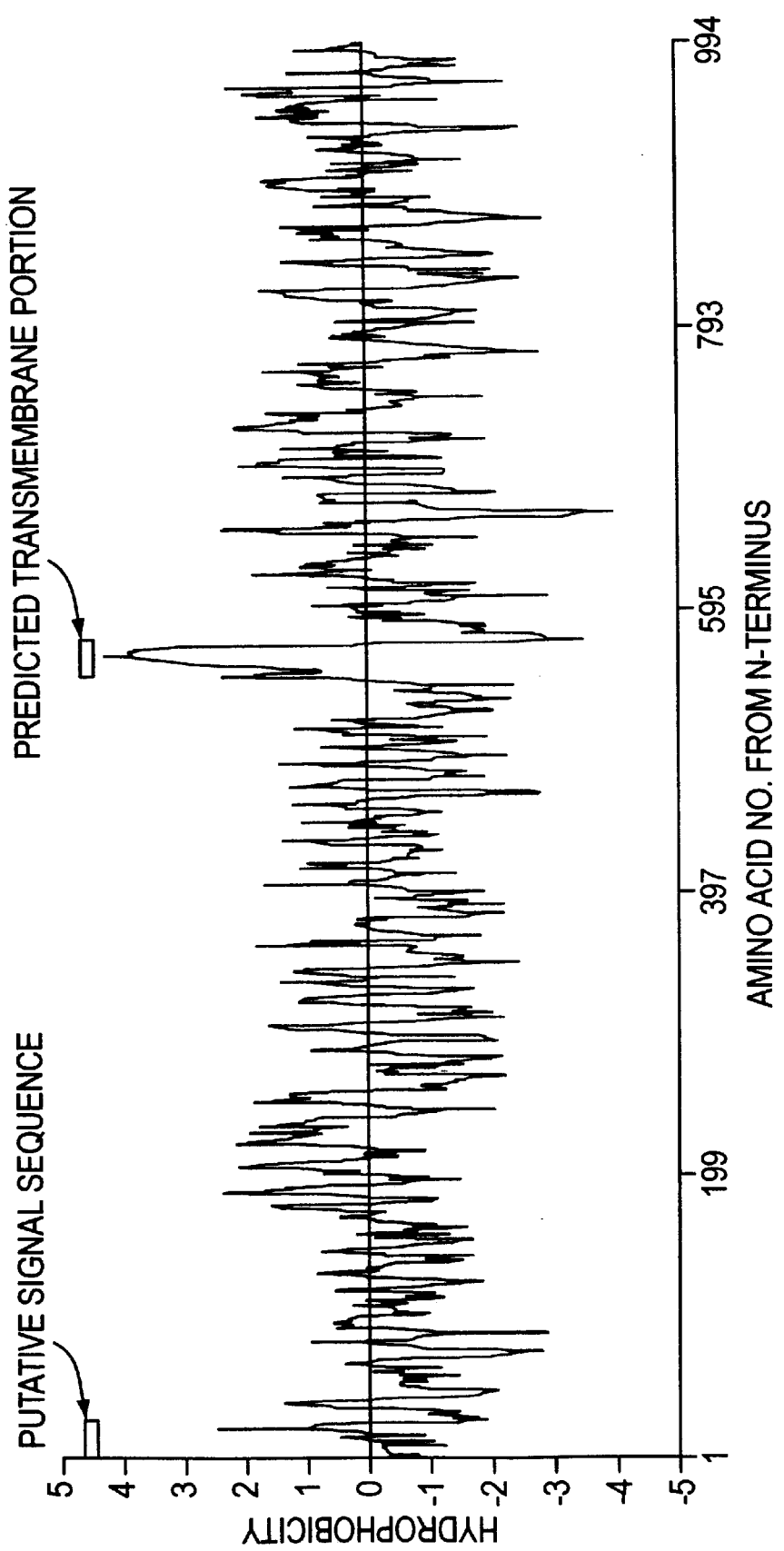
FIG. 4 shows a hydrophobicity profile for the polypeptide of protein p140 in the present invention
Figure 5:
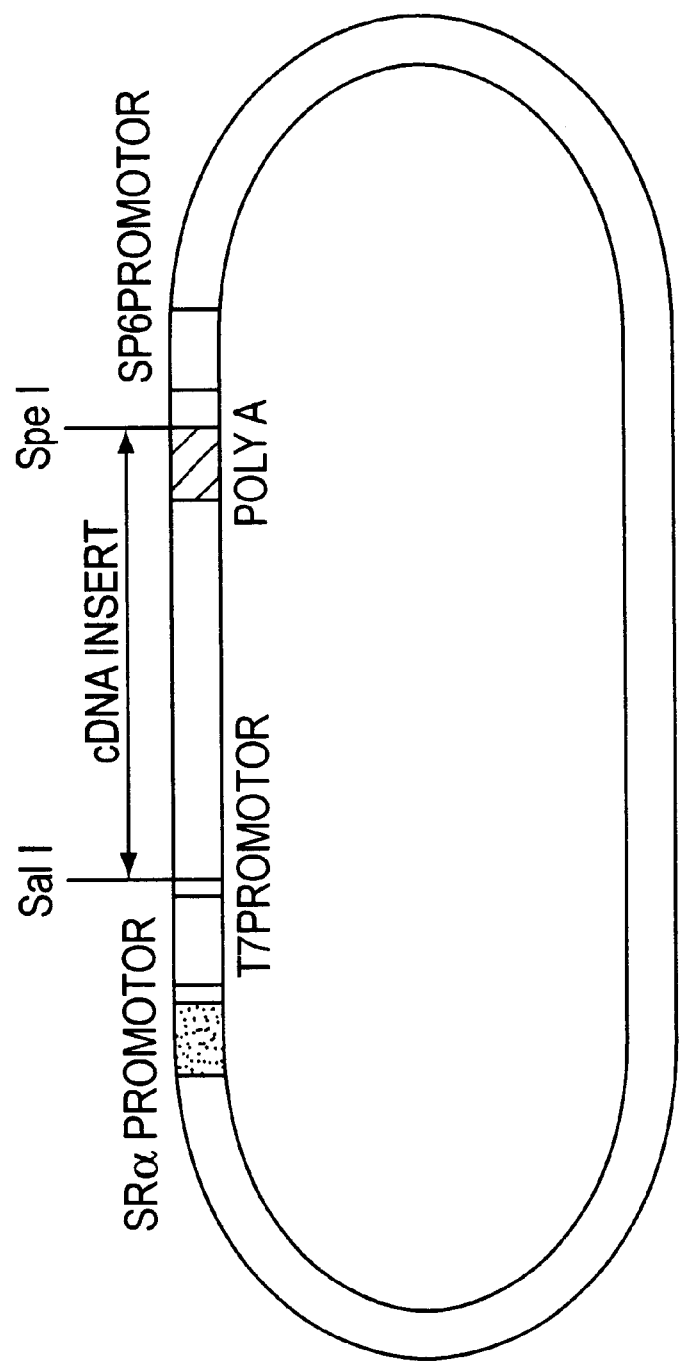
FIG. 5 shows the pUCSRαML2 vector.

Based on its hydrophobicity, protein p140 was further postulated to be a typical Type I membrane protein (FIG. 4 demarcates the zone with either high (+) or low (−) hydrophobicity).

All in all, the said p140 polypeptide is a typical membrane protein with 993 amino acids and the length of its ORF is 2982 bp. Furthermore, the estimated molecular weight of the said p140 polypeptide is 109,860 Da, and is 140 kD when evaluated from the bonds of its polysaccharide chain.

Example 14

Construction of Plasmid Vector for Using the Preparation of Expression Vector

As an expression vector, pUC-SRαML-1 (This vector is disclosed itself and preparation thereof in European Patent publication No. 559428 )derivative was used. This derivative was constructed to insert two kinds of fragments as shown below:

fragment T7 5' GTAATACGACTCACTATAGGG-GAGAGCT 3' (SEQ ID No. 8)

3' ACGTCATTATGCTGAGTGATATCCCCTC 5' (SEQ ID No. 9)

between PstI and SacI and fragment SP6 5' CTAGTCTATAGTGTCAC-CTAAATCGTGGGTAC 3' (SEQ ID No. 10)

3' AGATATCACAGTGGATTTAGCAC 5' (SEQ ID No. 11)

between SpeI and KpnI site in the multi-cloning site, respectively.

The pUC-SRαML1 vector was digested with PstI and SacI and the resulting digest was subjected to agarose gel electrophoresis to prepare and recover an about 4.1 kbp fragment and thereafter removing the 5'-end phosphoric acid group by BAP (bacterial alkaline phosphatase) treatment. The phosphorylated DNA fragment T7 was ligated with the thus prepared about 4.1 kbp fragment from pUC-SRαML1 to make them into a circular form. The resulting vector was, moreover, digested with SpeI and KpnI and the resulting digest was subjected to agarose gel electrophoresis to prepare and recover an about 4.1 kbp fragment and thereafter removing the 5'-end phosphoric acid group by BAP (bacterial alkaline phosphatase) treatment. The phosphorylated DNA fragment SP6 was ligated with the thus prepared about 4.1 kbp fragment to make them into a circular form. The plasmid vector constructed in this manner was named pUC-SRαML2 (See FIG. 3).

Example 15

Construction of Expression Vector

The primers X, Y and YH, that aneal to rat p140 cDNA, were synthesized. Sequences of primers X, Y and YH are as follows:
Primer X 5'- A ATA TAG TCG ACC ACC ATG GAG AAC CCC TAC GTT GGG CGA GCG A -3' (SEQ ID No. 12)
Primer Y 5'- CGG CGG ACT AGT TCA GAC CTG CAC GGG CAG TGT CTG G -3' (SEQ ID No. 13)
Primer YH 5'- GCC GCC ACT AGT TCA GTG GTG GTG GTG GTG GTG GAC CTG CAC GGG CAG TGT CTG G -3' (SEQ ID No. 14)

The plasmid containing cDNA of p140 was subjected to PCR using the thus synthesized oligonucleotides X and Y as templates. The thus obtained PCR fragment contains a sequence placed 5'-adjacent to the initiation codon, that is corresponding to Cozac sequence which is known among skilled in the art, and cDNA which encodes a protein molecule consisting of the p140 protein. The PCR fragment was digested with SaII-SpeI and the resulting digest was separated and purified and then inserted into the SaII-SpeI site of the pUC-SRαML2 prepared in Example 14 to obtain an expression vector pUC-SRαML2-p140-A.

Moreover, the plasmid containing cDNA of p140 was subjected to PCR using the synthesized oligonucleotides X and YH as templates. The thus obtained PCR fragment contains a sequence placed 5'-adjacent to the initiation codon, that is corresponding to Cozac sequence which is known among skilled in the art, and cDNA which encodes a protein molecule consisting of the p140 protein and six additional histidine (His) residues attached to its C-terminal end. The PCR fragment was digested with SaII-SpeI and the resulting digest was separated and purified and then inserted into the SaII-SpeI site of the pUC-SRαML2 prepared in Example 14 to obtain an expression vector pUC-SRαML2-p140-B.

Moreover, primer Z and ZH were synthesized. Sequences of primer Z and ZH are as follows: (These were adjoined to amino-terminal end of transmembrane region in cDNA.)
Primer Z 5'- CGG CGG ACT AGT TCA TGA GCC TCT TTC ACT CGT GGT CTC AAA CT -3' (SEQ ID No. 15)
Primer ZH 5'- GCC GCC ACT AGT TCA GTG GTG GTG GTG GTG GTG TGA GCC TCT TTC ACT CGT GGT CTC AAA CT -3' (SEQ ID No. 16)

The plasmid containing cDNA of p140 was subjected to PCR using the thus synthesized oligonucleotides X and Z as templates. The thus obtained PCR fragment contains a sequence placed 5'-adjacent to the initiation codon, that is corresponding to Cozac sequence which is known among skilled in the art, and cDNA which encodes a polypeptide consisting of the p140 protein extracellular part. The PCR fragment was digested with SaII and NotI and the resulting digest was separated and purified and then inserted into the SaII-SpeI site of the pUC-SRαML2 prepared in Example 14 to obtain an expression vector pUC-SRαML2-p140-C.

Moreover, the plasmid containing cDNA of p140 was subjected to PCR using the synthesized oligonucleotides X and ZH as templates. The thus obtained PCR fragment contains a sequence placed 5'-adjacent to the initiation codon, that is corresponding to Cozac sequence which is known among skilled in the art, and cDNA which encodes a polypeptide consisting of the p140 protein extracellular part and six additional histidine (His) residues attached to its C-terminal end. The PCR fragment was digested with SaII-SpeI and the resulting digest was separated and purified and then inserted into the SaII-SpeI site of the pUC-SRαML2 prepared in Example 14 to obtain an expression vector pUC-SRαML2-p140-D.

Each of the thus constructed pUC-SRαML2-p140-A, pUC-SRαML2-p140-B, pUC-SRαML2-p140-C and pUC-SRαML2-p140-D plasmids were transfected into an $E.$ $coli$ strain DH5, recovered from a 100 ml culture of the resulting transformant and then purified by CsCI density gradient centrifugation twice.

Example 16

Expression in COS Cells

Each of the plasmid DNA preparations pUC-SRαML2, pUC-SRαML2-p140-A, pUC-SRαML2-p140-B, pUC-SRαML2-p140-C and pUC-SRαML2-p140-D were introduced into COS-7 cells (Cell, 23, 175 (1981)) by means of the diethylaminoethyl (DEAE) dextran method (J. Immunology, 136, 4291 (1986)).

That is, about $1.8 \times 10_6$ COS-7 cells were inoculated into a 225 $cm^2$ capacity flask (manufactured by Corning) together with 50 ml of a liquid culture medium (Dulbecco's modified MEM medium supplemented with 10% decomplemented fetal bovine serum). After overnight incubation in a carbon dioxide incubator (37° C., 5% $CO_2$) and subsequent removal of the culture supernatant, 12 ml of a DNA cocktail (Dulbecco's modified MEM medium supplemented with 15 4g of each plasmid DNA, 50 mM Tris-HCI buffer (pH 7.4) and 400 μg/ml of DEAE-dextran) was added to each flask and culture was carried out for 3 hours at 37° C. in an atmosphere of 5% $CO_2$. Thereafter, the DNA cocktail was replaced by 15 ml of a chloroquine solution (Dulbecco's modified MEM medium supplemented with 150 μM chloroquine and 7% decomplemented fetal bovine serum), followed by additional 3 hours of culture.

After removing the chloroquine solution, the aforementioned liquid culture medium (50 ml) was added to each of the resulting flasks which were then incubated at 37° C. in an atmosphere of 5% $CO_2$ for 72 hours to find growth of the cells in each flask into almost monolayer form. After removing the culture supernatant, the cells in each flask were washed with a serum-free liquid culture medium (trade name, SFM-101; available from Nissui Pharmaceutical Co., Ltd.) and then supplied with 75 ml of the same serum-free liquid culture medium, and the culturing was continued for another 72 hours. Thereafter, the resulting culture supernatants were recovered and cells were lysed as represented in Example 1. These supernatants and cell lysates were filtered through a membrane filter (trade name, STERIVEX-GS; available from Millipore Corp.) to remove cell debris. The thus obtained culture supernatant samples were stored at 4° C. for future use. A The cell lysates of COS cells which have been transformed with plasmid containing the pUC- SRαML2-p140-A and pUC-SRαML2-p140-B inserts are expected to contain expressed mature protein moieties of polypeptides which correspond to p140 protein. And culture supernatants of COS cells which have been transformed with plasmid containing the pUC-SRαML2-p140-C and pUC-SRαML2-p140-D inserts are expected to contain secreted polypeptides which correspond to p140 protein extracellular part.

Example 17

Confirmation of Expression

A 2 ml portion of each of the culture supernatants of transformed COS cells obtained in Example 16 was concentrated to a volume of 100 ml using a centrifugal concentration filter (trade name, Centricon-10; available from Millipore Corp.). A 1 μl portion of each of the thus concentrated samples was mixed with the same volume of a loading buffer (0.125 M Tris-HCI buffer (pH 6.8), 4% sodium dodecyl sulfate and 30% glycerol) for SDS-PAGE (sodium dodecyl sulfate polyacrylamide gel electrophoresis) use, and the mixture was treated at 90° C. for 3 minutes and then subjected to SDS-PAGE.

In the case of the pUC-SRαML2-p140-B and pUC-SRαML2-p140-D proteins having His hexamer introduced to the C-terminus of the proteins, not only their corresponding cell lysates and COS cell culture supernatants but also their purified products were subjected to the SDS-PAGE analysis.

Purification of the protein was carried out by means of a metal chelate affinity chromatography (Biotechnology, 9, 273, (1991)), making use of the function of His to form complex compounds with various transition metal ions. That is, a culture supernatant (350 ml) or cell lysates (100 ml) obtained from COS cells was mixed with a sodium chloride aqueous solution in such an amount that the final concentration of the salt became 1 M, and the resulting mixture was applied to a column packed with 4 ml of a zinc-linked chelating Sepharose (trade name, Chelating Sepharose Fast-Flow; available from Pharmacia) to adsorb the protein to the resin. The column was washed with 50 mM phosphate buffer (pH 7.0) containing 1 M sodium chloride aqueous solution (40 ml), and the protein retained in the column was eluted with 50 mM phosphate buffer (pH 7.0) containing 1 M sodium chloride aqueous solution and 0.4 M imidazole. Thereafter, the resulting elute was concentrated to a volume of 100 1 μl, and a portion of the concentrated sample was subjected to SDS-PAGE analysis.

The SDS-PAGE analysis was carried out using a SDS 10/20 gradient gel and a product which corresponds to a molecular weight of p140 was detected in samples prepared from COS cells transfected pUC-SRαML2-p140-A and p140-B. Furthermore, a polypeptide which corresponds to a molecular weight of extracellular portion of p140 was detected in untreated and purified supernatants, not cell lysates, prepared from COS cells transfected pUC-SRαML2-p140-C and p140-D.

Formulation Example 1

The following components were admixed in convention method and punched out to obtain 100 tablets each containing 5 mg of active ingredient.

| | |
|---|---|
| Vitamin $K_5$ | 500.0 mg |
| Carboxymethylcellulose calcium | 200.0 mg |
| Magnesium stearate | 100.0 mg |
| Microcrystalline cellulose | 9.2 mg |

What is claimed is:

1. A composition for the treatment of diabetes comprising a therapeutically effective dose of a compound which induces phosphorylation of a tyrosine residue of protein p140, having the amino acid sequence shown in SEQ ID NO: 1 as an active ingredient.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 993 amino acids
      (B) TYPE: amino acid
      (D) TOPOLOGY: linear (ii) MOLECULE TYPE: protein (vi) ORIGINAL SOURCE:
      (A) ORGANISM: rat
      (F) TISSUE TYPE: skeletal muscle myoblast
      (H) CELL LINE: L6

(xi) SEQUENCE DESCRIPTION: SEQ ID NO:1:

```
Met Glu Asn Pro Tyr Val Gly Arg Ala Arg Ala Ala Ala Glu Arg Ala
 1               5                  10                  15

Ala Ala Glu Ala Thr Asn Ser Leu Ser Ile Leu Val Arg Pro Thr Ser
                20                  25                  30

Glu Gly Ser Arg Ile Asp Ser Glu Phe Val Glu Leu Ala Trp Thr Ser
                35                  40                  45
```

-continued

```
His Pro Glu Ser Gly Trp Glu Val Ser Ala Tyr Asp Glu Ala Met
    50                  55                  60
Asn Pro Ile Arg Thr Tyr Gln Val Cys Asn Val Arg Glu Ser Ser Gln
 65              70                  75                  80
Asn Asn Trp Leu Arg Thr Gly Phe Ile Trp Arg Glu Val Gln Arg
                85                  90                  95
Val Tyr Val Glu Leu Lys Phe Thr Val Arg Asp Cys Asn Ser Ile Pro
                100                 105                 110
Asn Ile Pro Gly Ser Cys Lys Glu Thr Phe Asn Leu Phe Tyr Tyr Glu
            115                 120                 125
Ala Asp Ser Asp Val Ala Ser Ala Ser Ser Pro Phe Trp Met Glu Asn
    130                 135                 140
Pro Tyr Val Lys Val Asp Thr Ile Ala Pro Asp Glu Ser Phe Ser Arg
145                 150                 155                 160
Leu Asp Ala Gly Arg Val Asn Thr Lys Val Arg Ser Phe Gly Pro Leu
                165                 170                 175
Ser Lys Ala Gly Phe Tyr Leu Ala Phe Gln Asp Gln Gly Ala Cys Met
                180                 185                 190
Ser Leu Ile Ser Val Arg Ala Phe Tyr Lys Lys Cys Ala Ser Thr Thr
            195                 200                 205
Ala Gly Phe Ala Leu Phe Pro Glu Thr Leu Thr Gly Ala Glu Pro Thr
    210                 215                 220
Ser Leu Val Ile Ala Pro Gly Thr Cys Ile Ala Asn Ala Val Glu Val
225                 230                 235                 240
Ser Val Pro Leu Lys Leu Tyr Cys Asn Gly Asp Gly Glu Trp Met Val
                245                 250                 255
Pro Val Gly Ala Cys Thr Cys Ala Thr Gly His Glu Pro Ala Ala Lys
                260                 265                 270
Glu Thr Gln Cys Arg Ala Cys Pro Gly Ser Tyr Lys Ala Lys Gln
            275                 280                 285
Gly Glu Gly Pro Cys Leu Pro Cys Pro Asn Ser Arg Thr Thr Ser
    290                 295                 300
Pro Ala Ala Ser Ile Cys Thr Cys His Asn Asn Phe Tyr Arg Ala Asp
305                 310                 315                 320
Ser Asp Thr Ala Asp Ser Ala Cys Thr Thr Val Pro Ser Pro Arg
            325                 330                 335
Gly Val Ile Ser Asn Val Asn Glu Thr Ser Leu Ile Leu Glu Trp Ser
            340                 345                 350
Glu Pro Arg Asp Leu Gly Gly Arg Asp Asp Leu Leu Tyr Asn Val Ile
    355                 360                 365
Cys Lys Lys Cys Arg Gly Ser Ser Gly Ala Gly Pro Ala Thr Cys
    370                 375                 380
Ser Arg Cys Asp Asp Asn Val Glu Phe Glu Pro Arg Gln Leu Gly Leu
385                 390                 395                 400
Thr Glu Arg Arg Val His Ile Ser His Leu Leu Ala His Thr Arg Tyr
                405                 410                 415
Thr Phe Glu Val Gln Ala Val Asn Gly Val Ser Gly Lys Ser Pro Leu
                420                 425                 430
Pro Pro Arg Tyr Ala Ala Val Asn Ile Thr Thr Asn Gln Ala Ala Pro
            435                 440                 445
Ser Glu Val Pro Thr Leu His Leu His Ser Ser Gly Ser Ser Leu
    450                 455                 460
```

```
Thr Leu Ser Trp Ala Pro Pro Glu Arg Pro Asn Gly Val Ile Leu Asp
465                 470                 475                 480

Tyr Glu Met Lys Tyr Phe Glu Lys Ser Lys Gly Ile Ala Ser Thr Val
            485                 490                 495

Thr Ser Gln Lys Asn Ser Val Gln Leu Asp Gly Leu Gln Pro Asp Ala
            500                 505                 510

Arg Tyr Val Val Gln Val Arg Ala Arg Thr Val Ala Gly Tyr Gly Gln
            515                 520                 525

Tyr Ser Arg Pro Ala Glu Phe Glu Thr Thr Ser Glu Arg Gly Ser Gly
530                 535                 540

Ala Gln Gln Leu Gln Glu Gln Leu Pro Leu Ile Val Gly Ser Thr Val
545                 550                 555                 560

Ala Gly Phe Val Phe Met Val Val Val Val Ile Ala Leu Val Cys
                565                 570                 575

Leu Arg Lys Gln Arg Gln Gly Pro Asp Ala Glu Tyr Thr Glu Lys Leu
            580                 585                 590

Gln Gln Tyr Val Ala Pro Arg Met Lys Val Tyr Ile Asp Pro Phe Thr
            595                 600                 605

Tyr Glu Asp Pro Asn Glu Ala Val Arg Glu Phe Ala Lys Glu Ile Asp
            610                 615                 620

Val Ser Cys Val Lys Ile Glu Glu Val Ile Gly Ala Gly Glu Phe Gly
625                 630                 635                 640

Glu Val Cys Arg Gly Arg Leu Lys Leu Pro Gly Arg Arg Glu Val Phe
                645                 650                 655

Val Ala Ile Lys Thr Leu Lys Val Gly Tyr Thr Glu Arg Gln Arg Arg
                660                 665                 670

Asp Phe Leu Ser Glu Ala Ser Ile Met Gly Gln Phe Asp His Pro Asn
            675                 680                 685

Ile Ile Arg Leu Glu Gly Val Val Thr Lys Ser Arg Pro Val Met Ile
            690                 695                 700

Leu Thr Glu Phe Met Glu Asn Cys Ala Leu Asp Ser Phe Leu Arg Leu
705                 710                 715                 720

Asn Asp Gly Gln Phe Thr Val Ile Gln Leu Val Gly Met Leu Arg Gly
                725                 730                 735

Ile Ala Ala Gly Met Lys Tyr Leu Ser Glu Met Asn Tyr Val His Arg
                740                 745                 750

Asp Leu Ala Ala Arg Asn Ile Leu Val Asn Ser Asn Leu Val Cys Lys
            755                 760                 765

Val Ser Asp Phe Gly Leu Ser Arg Phe Leu Glu Asp Asp Pro Ser Asp
770                 775                 780

Pro Thr Tyr Thr Ser Ser Leu Gly Gly Lys Ile Pro Ile Arg Trp Thr
785                 790                 795                 800

Ala Pro Glu Ala Ile Asp Tyr Arg Lys Phe Thr Ser Ala Ser Asp Val
                805                 810                 815

Trp Ser Tyr Gly Ile Val Met Trp Glu Val Met Ser Tyr Gly Glu Arg
                820                 825                 830

Pro Tyr Trp Asp Met Ser Asn Gln Asp Val Ile Asn Ala Val Glu Gln
            835                 840                 845

Asp Tyr Arg Leu Pro Pro Met Asp Cys Pro Ala Ala Leu His Gln
            850                 855                 860

Leu Met Leu Asp Cys Trp Val Arg Asp Arg Asn Leu Arg Pro Lys Phe
865                 870                 875                 880

Ser Gln Ile Val Asn Thr Leu Asp Lys Leu Ile Arg Asn Ala Ala Ser
```

-continued

```
                885                 890                  895
Leu Lys Val Ile Ala Ser Ala Pro Ser Gly Met Ser Gln Pro Leu Leu
                    900             905             910
Asp Arg Thr Val Pro Asp Tyr Thr Thr Phe Thr Thr Val Gly Asp Trp
            915                 920             925
Leu Asp Ala Ile Lys Met Gly Arg Tyr Lys Glu Ser Phe Val Gly Ala
        930             935             940
Gly Phe Ala Ser Phe Asp Leu Val Ala Gln Met Thr Ala Glu Asp Leu
945             950             955             960
Leu Arg Ile Gly Val Thr Leu Ala Gly His Gln Lys Lys Ile Leu Ser
                965             970             975
Ser Ile Gln Asp Met Arg Leu Gln Met Asn Gln Thr Leu Pro Val Gln
            980             985             990
Val
```

(2) INFORMATION FOR SEQ ID NO:2:

(i) SEQUENCE CHARACTERISTICS:
        (A) LENGTH: 2982 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: rat
        (F) TISSUE TYPE: skeletal muscle myoblast
        (H) CELL LINE: L6

(xi) SEQUENCE DESCRIPTION: SEQ ID NO:2:

```
ATGGAGAACC CCTACGTTGG GCGAGCGAGA GCAGCAGCGG AGCGAGCAGC GGCAGAAGCC      60
ACGAATTCAC TATCGATCCT GGTTCGGCCC ACCTCTGAAG GTTCCAGAAT CGATAGTGAA     120
TTCGTGGAGC TGGCATGGAC ATCTCATCCA GAGAGTGGGT GGGAAGAAGT GAGCGCCTAC     180
GATGAAGCCA TGAATCCTAT CCGCACGTAT CAGGTGTGTA ACGTGCGCGA GTCCAGCCAG     240
AACAACTGGC TGCGGACCGG TTTCATCTGG CGGCGGAAG TCCAGCGCGT CTACGTGGAG      300
CTGAAGTTTA CCGTGAGAGA TTGCAACAGC ATCCCCAACA TCCCTGGCTC CTGCAAGGAA     360
ACCTTCAACC TTTTTTACTA CGAGGCTGAT AGCGATGTGG CGTCAGCCTC CTCTCCCTTC     420
TGGATGGAGA ACCCCTACGT GAAAGTGGAC ACCATTGCGC CAGATGAGAG CTTCTCGCGG     480
CTAGACGCTG GGCGCGTTAA CACCAAAGTG CGCAGCTTCG GGCCGCTTTC CAAAGCCGGC     540
TTCTACTTGG CCTTCCAGGA CCAGGGTGCC TGCATGTCAC TCATCTCTGT GCGCGCCTTC     600
TACAAGAAGT GTGCATCCAC CACTGCAGGC TTCGCACTCT TCCCCGAGAC CCTCACGGGG     660
GCTGAGCCCA CTTCGCTGGT CATTGCCCCT GGCACCTGCA TCGCTAACGC TGTGGAGGTG     720
TCTGTACCGC TCAAGCTCTA CTGCAATGGC GACGGGGAGT GGATGGTGCC CGTTGGTGCC     780
TGCACCTGCG CTACTGGCCA TGAGCCAGCC GCCAAGGAGA CCCAGTGCCG CGCCTGTCCC     840
CCTGGGAGCT ACAAGGCAAA GCAAGGAGAG GGGCCCTGCC TCCCCTGTCC CCCCAATAGC     900
CGCACCACCT CGCCGGCTGC CAGCATCTGC ACCTGTCACA ATAATTTCTA CCGCGCAGAC     960
TCAGACACAG CGGACAGCGC CTGCACCACG GTGCCGTCTC CCCCCCGGGG TGTGATCTCC    1020
AATGTGAATG AGACCTCGCT GATCCTCGAG TGGAGTGAGC CCCGGGACCT TGGCGGACGA    1080
GATGACCTCC TTTATAATGT TATCTGTAAG AAGTGCCGTG GCAGCTCTGG GGCTGGAGGT    1140
CCGGCGACCT GTTCACGCTG TGATGACAAC GTGGAGTTCG AGCCCCGACA GCTGGGCCTG    1200
```

```
ACCGAGCGCC GGGTCCACAT CAGCCACCTG TTGGCCCACA CCCGCTACAC CTTTGAGGTG     1260

CAGGCTGTCA ACGGCGTCTC TGGCAAAAGC CCTTTGCCGC CCCGCTATGC AGCTGTGAAT     1320

ATCACCACCA ACCAGGCCGC CCCATCAGAA GTGCCTACGC TCCACTTGCA CAGCAGTTCA     1380

GGGAGCAGCC TGACCCTGTC CTGGGCACCC CCGGAGCGGC CTAACGGAGT CATCTTGGAC     1440

TATGAGATGA AGTACTTTGA GAAGAGTAAA GGCATCGCCT CCACTGTCAC CAGCCAGAAG     1500

AACTCTGTAC AACTGGACGG ACTGCAGCCC GACGCCCGCT ATGTAGTTCA GGTCCGGGCT     1560

CGCACAGTAG CAGGTTACGG ACAGTATAGC CGCCCAGCTG AGTTTGAGAC CACGAGTGAA     1620

AGAGGCTCAG GGGCCCAGCA GCTTCAAGAG CAGCTTCCCC TAATTGTGGG ATCCACCGTA     1680

GCTGGCTTTG TCTTCATGGT GGTCGTCGTG GTCATTGCTC TTGTCTGCCT CAGGAAGCAG     1740

CGCCAGGGCC CTGATGCAGA ATACACGGAG AAGTTGCAGC AATACGTTGC CCCCAGGATG     1800

AAAGTTTACA TTGACCCCTT TACCTACGAG GATCCCAATG AGGCCGTCCG AGAGTTCGCC     1860

AAGGAGATCG ATGTGTCCTG CGTCAAGATC GAGGAGGTGA TTGGAGCTGG GGAGTTTGGG     1920

GAAGTGTGCC GGGGTCGGCT GAAACTGCCC GGCCGCCGGG AGGTGTTCGT GGCCATCAAG     1980

ACACTGAAGG TGGGATACAC GGAGAGGCAG CGGCGGGACT TCCTGAGTGA GGCTTCCATC     2040

ATGGGTCAAT TTGACCATCC AAATATAATC CGTCTAGAGG GCGTGGTCAC CAAAAGTCGT     2100

CCAGTCATGA TCCTCACTGA GTTCATGGAG AACTGTGCCC TGGACTCCTT CCTACGGCTC     2160

AATGACGGGC AGTTCACAGT CATCCAGCTT GTGGGCATGT TGCGTGGCAT TGCTGCCGGC     2220

ATGAAGTACT TGTCTGAGAT GAACTACGTG CACCGTGACC TCGCTGCCCG CAACATCCTT     2280

GTCAACAGTA ACTTGGTCTG CAAAGTATCT GACTTTGGGC TCTCCCGCTT CCTGGAGGAC     2340

GACCCCTCAG ACCCCACCTA CACCAGCTCC CTGGGTGGGA AGATCCCTAT CCGTTGGACC     2400

GCCCCAGAGG CCATAGACTA TCGGAAGTTC ACGTCTGCCA GCGATGTCTG GAGCTACGGG     2460

ATCGTCATGT GGGAGGTCAT GAGCTACGGA GAGCGACCAT ACTGGGACAT GAGCAACCAG     2520

GATGTCATCA ATGCCGTAGA GCAAGACTAT CGGTTACCAC CCCCCATGGA CTGCCCAGCG     2580

GCGCTGCACC AGCTCATGCT GGACTGTTGG GTGCGGGACC GGAACCTCAG GCCCAAGTTC     2640

TCCCAAATCG TCAACACGCT AGACAAGCTT ATCCGCAATG CTGCCAGCCT CAAGGTCATC     2700

GCCAGTGCCC CATCTGGCAT GTCCCAGCCC CTCCTAGACC GCACGGTCCC AGATTATACG     2760

ACCTTCACGA CGGTGGGCGA CTGGCTAGAT GCCATCAAGA TGGGGAGGTA TAAAGAGAGC     2820

TTCGTCGGTG CGGGTTTTGC CTCCTTTGAC CTGGTGGCCC AGATGACTGC AGAAGATCTG     2880

CTAAGGATCG GGGTCACTTT GGCCGGCCAC CAGAAGAAGA TCCTCAGCAG TATCCAGGAC     2940

ATGCGGCTGC AGATGAACCA GACACTGCCC GTGCAGGTCT GA                       2982
```

(2) INFORMATION FOR SEQ ID NO:3:

(i) SEQUENCE CHARACTERISTICS:
        (A) LENGTH: 4027 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: rat
        (F) TISSUE TYPE: skeletal muscle myoblast
        (H) CELL LINE: L6

(xi) SEQUENCE DESCRIPTION: SEQ ID NO:3:

-continued

```
GAAAAATGAA GATCTATACC GACAGCAGAT CAGTGGCTGC CTGGGGCAAA GTTGGAGGGA    60

CATGTTATTT TGATTGTGAT GACATAATAC ATGCAAACAC GGCTAATCCT CTCAAAGCAT   120

ACACTTATAC ATGTGCAGCT TGGTATACAT AAATTATCCA TTACAAAACT ATGAGAAAGC   180

TATCACCACT ATGAAGCACC ACTCACAGTA TGTGAATCTC CACCCCCCTT CCACTGCTGA   240

GACACAGAAA TCCTAGACTG GATGGAGAAC CCCTACGTTG GGCGAGCGAG AGCAGCAGCG   300

GAGCGAGCAG CGGCAGAAGC CACGAATTCA CTATCGATCC TGGTTCGGCC CACCTCTGAA   360

GGTTCCAGAA TCGATAGTGA ATTCGTGGAG CTGGCATGGA CATCTCATCC AGAGAGTGGG   420

TGGGAAGAAG TGAGCGCCTA CGATGAAGCC ATGAATCCTA TCCGCACGTA TCAGGTGTGT   480

AACGTGCGCG AGTCCAGCCA GAACAACTGG CTGCGGACCG GTTTCATCTG GCGGCGGGAA   540

GTCCAGCGCG TCTACGTGGA GCTGAAGTTT ACCGTGAGAG ATTGCAACAG CATCCCCAAC   600

ATCCCTGGCT CCTGCAAGGA AACCTTCAAC CTTTTTTACT ACGAGGCTGA TAGCGATGTG   660

GCGTCAGCCT CCTCTCCCTT CTGGATGGAG AACCCCTACG TGAAAGTGGA CACCATTGCG   720

CCAGATGAGA GCTTCTCGCG GCTAGACGCT GGGCGCGTTA ACACCAAAGT GCGCAGCTTC   780

GGGCCGCTTT CCAAAGCCGG CTTCTACTTG GCCTTCCAGG ACCAGGGTGC CTGCATGTCA   840

CTCATCTCTG TGCGCGCCTT CTACAAGAAG TGTGCATCCA CCACTGCAGG CTTCGCACTC   900

TTCCCCGAGA CCCTCACGGG GGCTGAGCCC ACTTCGCTGG TCATTGCCCC TGGCACCTGC   960

ATCGCTAACG CTGTGGAGGT GTCTGTACCG CTCAAGCTCT ACTGCAATGG CGACGGGGAG  1020

TGGATGGTGC CCGTTGGTGC CTGCACCTGC GCTACTGGCC ATGAGCCAGC CGCCAAGGAG  1080

ACCCAGTGCC GCGCCTGTCC CCCTGGGAGC TACAAGGCAA AGCAAGGAGA GGGGCCCTGC  1140

CTCCCCTGTC CCCCCAATAG CCGCACCACC TCGCCGGCTG CCAGCATCTG CACCTGTCAC  1200

AATAATTTCT ACCGCGCAGA CTCAGACACA GCGGACAGCG CCTGCACCAC GGTGCCGTCT  1260

CCCCCCCGGG GTGTGATCTC CAATGTGAAT GAGACCTCGC TGATCCTCGA GTGGAGTGAG  1320

CCCCGGGACC TTGGCGGACG AGATGACCTC CTTTATAATG TTATCTGTAA GAAGTGCCGT  1380

GGCAGCTCTG GGGCTGGAGG TCCGGCGACC TGTTCACGCT GTGATGACAA CGTGGAGTTC  1440

GAGCCCCGAC AGCTGGGCCT GACCGAGCGC CGGGTCCACA TCAGCCACCT GTTGGCCCAC  1500

ACCCGCTACA CCTTTGAGGT GCAGGCTGTC AACGGCGTCT CTGGCAAAAG CCCTTTGCCG  1560

CCCCGCTATG CAGCTGTGAA TATCACCACC AACCAGGCCG CCCCATCAGA AGTGCCTACG  1620

CTCCACTTGC ACAGCAGTTC AGGGAGCAGC CTGACCCTGT CCTGGGCACC CCCGGAGCGG  1680

CCTAACGGAG TCATCTTGGA CTATGAGATG AAGTACTTTG AGAAGAGTAA AGGCATCGCC  1740

TCCACTGTCA CCAGCCAGAA GAACTCTGTA CAACTGGACG GACTGCAGCC CGACGCCCGC  1800

TATGTAGTTC AGGTCCGGGC TCGCACAGTA GCAGGTTACG GACAGTATAG CCGCCCAGCT  1860

GAGTTTGAGA CCACGAGTGA AAGAGGCTCA GGGGCCCAGC AGCTTCAAGA GCAGCTTCCC  1920

CTAATTGTGG GATCCACCGT AGCTGGCTTT GTCTTCATGG TGGTCGTCGT GGTCATTGCT  1980

CTTGTCTGCC TCAGGAAGCA GCGCCAGGGC CCTGATGCAG AATACACGGA GAAGTTGCAG  2040

CAATACGTTG CCCCCAGGAT GAAAGTTTAC ATTGACCCCT TTACCTACGA GGATCCCAAT  2100

GAGGCCGTCC GAGAGTTCGC CAAGGAGATC GATGTGTCCT GCGTCAAGAT CGAGGAGGTG  2160

ATTGGAGCTG GGGAGTTTGG GGAAGTGTGC CGGGGTCGGC TGAAACTGCC CGGCCGCCGG  2220

GAGGTGTTCG TGGCCATCAA GACACTGAAG GTGGGATACA CGGAGAGGCA GCGGCGGGAC  2280

TTCCTGAGTG AGGCTTCCAT CATGGGTCAA TTTGACCATC CAAATATAAT CCGTCTAGAG  2340

GGCGTGGTCA CCAAAAGTCG TCCAGTCATG ATCCTCACTG AGTTCATGGA GAACTGTGCC  2400
```

```
CTGGACTCCT TCCTACGGCT CAATGACGGG CAGTTCACAG TCATCCAGCT TGTGGGCATG    2460

TTGCGTGGCA TTGCTGCCGG CATGAAGTAC TTGTCTGAGA TGAACTACGT GCACCGTGAC    2520

CTCGCTGCCC GCAACATCCT TGTCAACAGT AACTTGGTCT GCAAAGTATC TGACTTTGGG    2580

CTCTCCCGCT TCCTGGAGGA CGACCCCTCA GACCCCACCT ACACCAGCTC CCTGGGTGGG    2640

AAGATCCCTA TCCGTTGGAC CGCCCCAGAG GCCATAGACT ATCGGAAGTT CACGTCTGCC    2700

AGCGATGTCT GGAGCTACGG GATCGTCATG TGGGAGGTCA TGAGCTACGG AGAGCGACCA    2760

TACTGGGACA TGAGCAACCA GGATGTCATC AATGCCGTAG AGCAAGACTA TCGGTTACCA    2820

CCCCCCATGG ACTGCCCAGC GGCGCTGCAC CAGCTCATGC TGGACTGTTG GGTGCGGGAC    2880

CGGAACCTCA GGCCCAAGTT CTCCCAAATC GTCAACACGC TAGACAAGCT TATCCGCAAT    2940

GCTGCCAGCC TCAAGGTCAT CGCCAGTGCC CCATCTGGCA TGTCCCAGCC CCTCCTAGAC    3000

CGCACGGTCC CAGATTATAC GACCTTCACG ACGGTGGGCG ACTGGCTAGA TGCCATCAAG    3060

ATGGGGAGGT ATAAAGAGAG CTTCGTCGGT GCGGGTTTTG CCTCCTTTGA CCTGGTGGCC    3120

CAGATGACTG CAGAAGATCT GCTAAGGATC GGGGTCACTT TGGCCGGCCA CCAGAAGAAG    3180

ATCCTCAGCA GTATCCAGGA CATGCGGCTG CAGATGAACC AGACACTGCC CGTGCAGGTC    3240

TGACGCTCAG CTCCAGCGAG GGGCGTGGCC CCCCGGGACT GCACAAGGAT TCTGACCAGC    3300

CAGCTGGACT TTTGGATACC TGGCCTTTGG CTGTGGCCCA GAAGACAGAA GTTCGGGGGA    3360

GAACCCTAGC TGTGACTTCT CCAAGCCTGT GCTCCCTCCC AGGAAGTGTG CCCCAAACCT    3420

CTTCATATTG AAGATGGATT AGAAGAGGGG GTGATATCCC CTCCCCAGAT GCCTCAGGGC    3480

CCAGGCCTGC CTGCTCTCCA GTCGGGGATC TTCACAACTC AGATTTGGTT GTGCTTCAGT    3540

AGTGGAGGTC CTGGTAGGGT CGGGTGGGGA TAAGCCTGGG TTCTTCAGGC CCCAGCCCTG    3600

GCAGGGGTCT GACCCCAGCA GGTAAGCAGA GAGTACTCCC TCCCCAGGAA GTGGAGGAGG    3660

GGACTCTGGG AATGGGGAAA TATGGTGCCC CATCCTGAAG CCAGCTGGTA CCTCCAGTTT    3720

GCACAGGGAC TTGTTGGGGG CTGAGGGCCC TGCCTACCCT TGGTGCTGTC ATAAAAGGGC    3780

AGGCGGGAGC GGGCTGAGAA ACAGCCTGTG CCTCCCAGAG ACTGACTCAG AGAGCCAGAG    3840

ACGTGTGTGT GTGTGTGTGT GTGTGTGTGT GTGTGTGTGT GTGTGTGAAA GACGGGGGTG    3900

GGGTATGTAT GCGTGTGTTG TGCACATGCT TGCCTGCACA GAGAGCATGA GTGTGTACAA    3960

GCTTAGCCCT GTGCCCTGTA GTGGGGCCAG CTGGGCAGAC AGCGAAATAA AAGGCAATAA    4020

GTTGAAA                                                              4027
```

(2) INFORMATION FOR SEQ ID NO:4:

(i) SEQUENCE CHARACTERISTICS:
        (A) LENGTH: 4027 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: rat
        (F) TISSUE TYPE: skeletal muscle myoblast
        (H) CELL LINE: L6

(ix) FEATURE:
        (A) NAME/KEY: CDS
        (B) LOCATION: 262..3243
        (C) IDENTIFICATION METHOD: by similarity to some other pattern (xi) SEQUENCE DESCRIPTION: SEQ ID NO:4:

```
GAAAAATGAA GATCTATACC GACAGCAGAT CAGTGGCTGC CTGGGGCAAA GTTGGAGGGA         60

CATGTTATTT TGATTGTGAT GACATAATAC ATGCAAACAC GGCTAATCCT CTCAAAGCAT        120

ACACTTATAC ATGTGCAGCT TGGTATACAT AAATTATCCA TTACAAAACT ATGAGAAAGC        180

TATCACCACT ATGAAGCACC ACTCACAGTA TGTGAATCTC CACCCCCCTT CCACTGCTGA        240

GACACAGAAA TCCTAGACTG G ATG GAG AAC CCC TAC GTT GGG CGA GCG AGA          291
                        Met Glu Asn Pro Tyr Val Gly Arg Ala Arg
                         1               5                  10

GCA GCA GCG GAG CGA GCA GCG GAA GCC ACG AAT TCA CTA TCG ATC              339
Ala Ala Ala Glu Arg Ala Ala Glu Ala Thr Asn Ser Leu Ser Ile
                15                  20                  25

CTG GTT CGG CCC ACC TCT GAA GGT TCC AGA ATC GAT AGT GAA TTC GTG          387
Leu Val Arg Pro Thr Ser Glu Gly Ser Arg Ile Asp Ser Glu Phe Val
            30                  35                  40

GAG CTG GCA TGG ACA TCT CAT CCA GAG AGT GGG TGG GAA GAA GTG AGC          435
Glu Leu Ala Trp Thr Ser His Pro Glu Ser Gly Trp Glu Glu Val Ser
                45                  50                  55

GCC TAC GAT GAA GCC ATG AAT CCT ATC CGC ACG TAT CAG GTG TGT AAC          483
Ala Tyr Asp Glu Ala Met Asn Pro Ile Arg Thr Tyr Gln Val Cys Asn
            60                  65                  70

GTG CGC GAG TCC AGC CAG AAC AAC TGG CTG CGG ACC GGT TTC ATC TGG          531
Val Arg Glu Ser Ser Gln Asn Asn Trp Leu Arg Thr Gly Phe Ile Trp
 75                  80                  85                  90

CGG CGG GAA GTC CAG CGC GTC TAC GTG GAG CTG AAG TTT ACC GTG AGA          579
Arg Arg Glu Val Gln Arg Val Tyr Val Glu Leu Lys Phe Thr Val Arg
                95                 100                 105

GAT TGC AAC AGC ATC CCC AAC ATC CCT GGC TCC TGC AAG GAA ACC TTC          627
Asp Cys Asn Ser Ile Pro Asn Ile Pro Gly Ser Cys Lys Glu Thr Phe
            110                 115                 120

AAC CTT TTT TAC TAC GAG GCT GAT AGC GAT GTG GCG TCA GCC TCC TCT          675
Asn Leu Phe Tyr Tyr Glu Ala Asp Ser Asp Val Ala Ser Ala Ser Ser
            125                 130                 135

CCC TTC TGG ATG GAG AAC CCC TAC GTG AAA GTG GAC ACC ATT GCG CCA          723
Pro Phe Trp Met Glu Asn Pro Tyr Val Lys Val Asp Thr Ile Ala Pro
        140                 145                 150

GAT GAG AGC TTC TCG CGG CTA GAC GCT GGG CGC GTT AAC ACC AAA GTG          771
Asp Glu Ser Phe Ser Arg Leu Asp Ala Gly Arg Val Asn Thr Lys Val
155                 160                 165                 170

CGC AGC TTC GGG CCG CTT TCC AAA GCC GGC TTC TAC TTG GCC TTC CAG          819
Arg Ser Phe Gly Pro Leu Ser Lys Ala Gly Phe Tyr Leu Ala Phe Gln
                175                 180                 185

GAC CAG GGT GCC TGC ATG TCA CTC ATC TCT GTG CGC GCC TTC TAC AAG          867
Asp Gln Gly Ala Cys Met Ser Leu Ile Ser Val Arg Ala Phe Tyr Lys
            190                 195                 200

AAG TGT GCA TCC ACC ACT GCA GGC TTC GCA CTC TTC CCC GAG ACC CTC          915
Lys Cys Ala Ser Thr Thr Ala Gly Phe Ala Leu Phe Pro Glu Thr Leu
            205                 210                 215

ACG GGG GCT GAG CCC ACT TCG CTG GTC ATT GCC CCT GGC ACC TGC ATC          963
Thr Gly Ala Glu Pro Thr Ser Leu Val Ile Ala Pro Gly Thr Cys Ile
        220                 225                 230

GCT AAC GCT GTG GAG GTG TCT GTA CCG CTC AAG CTC TAC TGC AAT GGC         1011
Ala Asn Ala Val Glu Val Ser Val Pro Leu Lys Leu Tyr Cys Asn Gly
235                 240                 245                 250

GAC GGG GAG TGG ATG GTG CCC GTT GGT GCC TGC ACC TGC GCT ACT GGC         1059
Asp Gly Glu Trp Met Val Pro Val Gly Ala Cys Thr Cys Ala Thr Gly
                255                 260                 265

CAT GAG CCA GCC GCC AAG GAG ACC CAG TGC CGC GCC TGT CCC CCT GGG         1107
His Glu Pro Ala Ala Lys Glu Thr Gln Cys Arg Ala Cys Pro Pro Gly
```

```
                        270                    275                    280
AGC TAC AAG GCA AAG CAA GGA GAG GGG CCC TGC CTC CCC TGT CCC CCC            1155
Ser Tyr Lys Ala Lys Gln Gly Glu Gly Pro Cys Leu Pro Cys Pro Pro
            285                    290                    295

AAT AGC CGC ACC ACC TCG CCG GCT GCC AGC ATC TGC ACC TGT CAC AAT            1203
Asn Ser Arg Thr Thr Ser Pro Ala Ala Ser Ile Cys Thr Cys His Asn
300                 305                    310

AAT TTC TAC CGC GCA GAC TCA GAC ACA GCG GAC AGC GCC TGC ACC ACG            1251
Asn Phe Tyr Arg Ala Asp Ser Asp Thr Ala Asp Ser Ala Cys Thr Thr
315                 320                    325                    330

GTG CCG TCT CCC CCC CGG GGT GTG ATC TCC AAT GTG AAT GAG ACC TCG            1299
Val Pro Ser Pro Pro Arg Gly Val Ile Ser Asn Val Asn Glu Thr Ser
                335                    340                    345

CTG ATC CTC GAG TGG AGT GAG CCC CGG GAC CTT GGC GGA CGA GAT GAC            1347
Leu Ile Leu Glu Trp Ser Glu Pro Arg Asp Leu Gly Gly Arg Asp Asp
            350                    355                    360

CTC CTT TAT AAT GTT ATC TGT AAG AAG TGC CGT GGC AGC TCT GGG GCT            1395
Leu Leu Tyr Asn Val Ile Cys Lys Lys Cys Arg Gly Ser Ser Gly Ala
            365                    370                    375

GGA GGT CCG GCG ACC TGT TCA CGC TGT GAT GAC AAC GTG GAG TTC GAG            1443
Gly Gly Pro Ala Thr Cys Ser Arg Cys Asp Asp Asn Val Glu Phe Glu
        380                    385                    390

CCC CGA CAG CTG GGC CTG ACC GAG CGC CGG GTC CAC ATC AGC CAC CTG            1491
Pro Arg Gln Leu Gly Leu Thr Glu Arg Arg Val His Ile Ser His Leu
395                 400                    405                    410

TTG GCC CAC ACC CGC TAC ACC TTT GAG GTG CAG GCT GTC AAC GGC GTC            1539
Leu Ala His Thr Arg Tyr Thr Phe Glu Val Gln Ala Val Asn Gly Val
                415                    420                    425

TCT GGC AAA AGC CCT TTG CCG CCC CGC TAT GCA GCT GTG AAT ATC ACC            1587
Ser Gly Lys Ser Pro Leu Pro Pro Arg Tyr Ala Ala Val Asn Ile Thr
            430                    435                    440

ACC AAC CAG GCC GCC CCA TCA GAA GTG CCT ACG CTC CAC TTG CAC AGC            1635
Thr Asn Gln Ala Ala Pro Ser Glu Val Pro Thr Leu His Leu His Ser
            445                    450                    455

AGT TCA GGG AGC AGC CTG ACC CTG TCC TGG GCA CCC CCG GAG CGG CCT            1683
Ser Ser Gly Ser Ser Leu Thr Leu Ser Trp Ala Pro Pro Glu Arg Pro
        460                    465                    470

AAC GGA GTC ATC TTG GAC TAT GAG ATG AAG TAC TTT GAG AAG AGT AAA            1731
Asn Gly Val Ile Leu Asp Tyr Glu Met Lys Tyr Phe Glu Lys Ser Lys
475                 480                    485                    490

GGC ATC GCC TCC ACT GTC ACC AGC CAG AAG AAC TCT GTA CAA CTG GAC            1779
Gly Ile Ala Ser Thr Val Thr Ser Gln Lys Asn Ser Val Gln Leu Asp
                495                    500                    505

GGA CTG CAG CCC GAC GCC CGC TAT GTA GTT CAG GTC CGG GCT CGC ACA            1827
Gly Leu Gln Pro Asp Ala Arg Tyr Val Val Gln Val Arg Ala Arg Thr
            510                    515                    520

GTA GCA GGT TAC GGA CAG TAT AGC CGC CCA GCT GAG TTT GAG ACC ACG            1875
Val Ala Gly Tyr Gly Gln Tyr Ser Arg Pro Ala Glu Phe Glu Thr Thr
            525                    530                    535

AGT GAA AGA GGC TCA GGG GCC CAG CAG CTT CAA GAG CAG CTT CCC CTA            1923
Ser Glu Arg Gly Ser Gly Ala Gln Gln Leu Gln Glu Gln Leu Pro Leu
            540                    545                    550

ATT GTG GGA TCC ACC GTA GCT GGC TTT GTC TTC ATG GTG GTC GTC GTG            1971
Ile Val Gly Ser Thr Val Ala Gly Phe Val Phe Met Val Val Val Val
555                 560                    565                    570

GTC ATT GCT CTT GTC TGC CTC AGG AAG CAG CGC CAG GGC CCT GAT GCA            2019
Val Ile Ala Leu Val Cys Leu Arg Lys Gln Arg Gln Gly Pro Asp Ala
                575                    580                    585

GAA TAC ACG GAG AAG TTG CAG CAA TAC GTT GCC CCC AGG ATG AAA GTT            2067
Glu Tyr Thr Glu Lys Leu Gln Gln Tyr Val Ala Pro Arg Met Lys Val
```

```
                                                            -continued

Glu Tyr Thr Glu Lys Leu Gln Gln Tyr Val Ala Pro Arg Met Lys Val
            590                 595                 600
TAC ATT GAC CCC TTT ACC TAC GAG GAT CCC AAT GAG GCC GTC CGA GAG      2115
Tyr Ile Asp Pro Phe Thr Tyr Glu Asp Pro Asn Glu Ala Val Arg Glu
                605                 610                 615
TTC GCC AAG GAG ATC GAT GTG TCC TGC GTC AAG ATC GAG GAG GTG ATT      2163
Phe Ala Lys Glu Ile Asp Val Ser Cys Val Lys Ile Glu Glu Val Ile
        620                 625                 630
GGA GCT GGG GAG TTT GGG GAA GTG TGC CGG GGT CGG CTG AAA CTG CCC      2211
Gly Ala Gly Glu Phe Gly Glu Val Cys Arg Gly Arg Leu Lys Leu Pro
635                 640                 645                 650
GGC CGC CGG GAG GTG TTC GTG GCC ATC AAG ACA CTG AAG GTG GGA TAC      2259
Gly Arg Arg Glu Val Phe Val Ala Ile Lys Thr Leu Lys Val Gly Tyr
                655                 660                 665
ACG GAG AGG CAG CGG CGG GAC TTC CTG AGT GAG GCT TCC ATC ATG GGT      2307
Thr Glu Arg Gln Arg Arg Asp Phe Leu Ser Glu Ala Ser Ile Met Gly
                670                 675                 680
CAA TTT GAC CAT CCA AAT ATA ATC CGT CTA GAG GGC GTG GTC ACC AAA      2355
Gln Phe Asp His Pro Asn Ile Ile Arg Leu Glu Gly Val Val Thr Lys
                685                 690                 695
AGT CGT CCA GTC ATG ATC CTC ACT GAG TTC ATG GAG AAC TGT GCC CTG      2403
Ser Arg Pro Val Met Ile Leu Thr Glu Phe Met Glu Asn Cys Ala Leu
        700                 705                 710
GAC TCC TTC CTA CGG CTC AAT GAC GGG CAG TTC ACA GTC ATC CAG CTT      2451
Asp Ser Phe Leu Arg Leu Asn Asp Gly Gln Phe Thr Val Ile Gln Leu
715                 720                 725                 730
GTG GGC ATG TTG CGT GGC ATT GCT GCC GGC ATG AAG TAC TTG TCT GAG      2499
Val Gly Met Leu Arg Gly Ile Ala Ala Gly Met Lys Tyr Leu Ser Glu
                735                 740                 745
ATG AAC TAC GTG CAC CGT GAC CTC GCT GCC CGC AAC ATC CTT GTC AAC      2547
Met Asn Tyr Val His Arg Asp Leu Ala Ala Arg Asn Ile Leu Val Asn
                750                 755                 760
AGT AAC TTG GTC TGC AAA GTA TCT GAC TTT GGG CTC TCC CGC TTC CTG      2595
Ser Asn Leu Val Cys Lys Val Ser Asp Phe Gly Leu Ser Arg Phe Leu
        765                 770                 775
GAG GAC GAC CCC TCA GAC CCC ACC TAC ACC AGC TCC CTG GGT GGG AAG      2643
Glu Asp Asp Pro Ser Asp Pro Thr Tyr Thr Ser Ser Leu Gly Gly Lys
780                 785                 790
ATC CCT ATC CGT TGG ACC GCC CCA GAG GCC ATA GAC TAT CGG AAG TTC      2691
Ile Pro Ile Arg Trp Thr Ala Pro Glu Ala Ile Asp Tyr Arg Lys Phe
795                 800                 805                 810
ACG TCT GCC AGC GAT GTC TGG AGC TAC GGG ATC GTC ATG TGG GAG GTC      2739
Thr Ser Ala Ser Asp Val Trp Ser Tyr Gly Ile Val Met Trp Glu Val
                815                 820                 825
ATG AGC TAC GGA GAG CGA CCA TAC TGG GAC ATG AGC AAC CAG GAT GTC      2787
Met Ser Tyr Gly Glu Arg Pro Tyr Trp Asp Met Ser Asn Gln Asp Val
                830                 835                 840
ATC AAT GCC GTA GAG CAA GAC TAT CGG TTA CCA CCC CCC ATG GAC TGC      2835
Ile Asn Ala Val Glu Gln Asp Tyr Arg Leu Pro Pro Pro Met Asp Cys
                845                 850                 855
CCA GCG GCG CTG CAC CAG CTC ATG CTG GAC TGT TGG GTG CGG GAC CGG      2883
Pro Ala Ala Leu His Gln Leu Met Leu Asp Cys Trp Val Arg Asp Arg
        860                 865                 870
AAC CTC AGG CCC AAG TTC TCC CAA ATC GTC AAC ACG CTA GAC AAG CTT      2931
Asn Leu Arg Pro Lys Phe Ser Gln Ile Val Asn Thr Leu Asp Lys Leu
875                 880                 885                 890
ATC CGC AAT GCT GCC AGC CTC AAG GTC ATC GCC AGT GCC CCA TCT GGC      2979
Ile Arg Asn Ala Ala Ser Leu Lys Val Ile Ala Ser Ala Pro Ser Gly
                895                 900                 905
```

```
ATG TCC CAG CCC CTC CTA GAC CGC ACG GTC CCA GAT TAT ACG ACC TTC      3027
Met Ser Gln Pro Leu Leu Asp Arg Thr Val Pro Asp Tyr Thr Thr Phe
        910                 915                 920

ACG ACG GTG GGC GAC TGG CTA GAT GCC ATC AAG ATG GGG AGG TAT AAA      3075
Thr Thr Val Gly Asp Trp Leu Asp Ala Ile Lys Met Gly Arg Tyr Lys
            925                 930                 935

GAG AGC TTC GTC GGT GCG GGT TTT GCC TCC TTT GAC CTG GTG GCC CAG      3123
Glu Ser Phe Val Gly Ala Gly Phe Ala Ser Phe Asp Leu Val Ala Gln
        940                 945                 950

ATG ACT GCA GAA GAT CTG CTA AGG ATC GGG GTC ACT TTG GCC GGC CAC      3171
Met Thr Ala Glu Asp Leu Leu Arg Ile Gly Val Thr Leu Ala Gly His
955                 960                 965                 970

CAG AAG AAG ATC CTC AGC AGT ATC CAG GAC ATG CGG CTG CAG ATG AAC      3219
Gln Lys Lys Ile Leu Ser Ser Ile Gln Asp Met Arg Leu Gln Met Asn
                975                 980                 985

CAG ACA CTG CCC GTG CAG GTC TGACGCTCAG CTCCAGCGAG GGGCGTGGCC         3270
Gln Thr Leu Pro Val Gln Val
                990

CCCCGGGACT GCACAAGGAT TCTGACCAGC CAGCTGGACT TTTGGATACC TGGCCTTTGG    3330

CTGTGGCCCA GAAGACAGAA GTTCGGGGGA GAACCCTAGC TGTGACTTCT CCAAGCCTGT    3390

GCTCCCTCCC AGGAAGTGTG CCCCAAACCT CTTCATATTG AAGATGGATT AGAAGAGGGG    3450

GTGATATCCC CTCCCCAGAT GCCTCAGGGC CCAGGCCTGC CTGCTCTCCA GTCGGGGATC    3510

TTCACAACTC AGATTTGGTT GTGCTTCAGT AGTGGAGGTC CTGGTAGGGT CGGGTGGGGA    3570

TAAGCCTGGG TTCTTCAGGC CCCAGCCCTG GCAGGGGTCT GACCCCAGCA GGTAAGCAGA    3630

GAGTACTCCC TCCCCAGGAA GTGGAGGAGG GGACTCTGGG AATGGGGAAA TATGGTGCCC    3690

CATCCTGAAG CCAGCTGGTA CCTCCAGTTT GCACAGGGAC TTGTTGGGGG CTGAGGGCCC    3750

TGCCTACCCT TGGTGCTGTC ATAAAAGGGC AGGCGGGAGC GGGCTGAGAA ACAGCCTGTG    3810

CCTCCCAGAG ACTGACTCAG AGAGCCAGAG ACGTGTGTGT GTGTGTGTGT GTGTGTGTGT    3870

GTGTGTGTGT GTGTGTGAAA GACGGGGGTG GGGTATGTAT GCGTGTGTTG TGCACATGCT    3930

TGCCTGCACA GAGAGCATGA GTGTGTACAA GCTTAGCCCT GTGCCCTGTA GTGGGGCCAG    3990

CTGGGCAGAC AGCGAAATAA AAGGCAATAA GTTGAAA                             4027
```

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: protein (vi) ORIGINAL SOURCE:
        (A) ORGANISM: rat
        (F) TISSUE TYPE: skeletal muscle myoblast
        (H) CELL LINE: L6

(xi) SEQUENCE DESCRIPTION: SEQ ID NO:5:

```
Val Ile Gly Ala Gly Glu Phe Gly Glu Val Cys
1               5                   10
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: protein (vi) ORIGINAL SOURCE:
              (A) ORGANISM: rat
              (F) TISSUE TYPE: skeletal muscle myoblast
              (H) CELL LINE: L6

(xi) SEQUENCE DESCRIPTION: SEQ ID NO:6:

Asn Ile Leu Val Asn Ser Asn Leu Val Cys
1               5                   10

(2) INFORMATION FOR SEQ ID NO:7:

(i) SEQUENCE CHARACTERISTICS:
              (A) LENGTH: 5 amino acids
              (B) TYPE: amino acid
              (D) TOPOLOGY: linear (ii) MOLECULE TYPE: protein (vi) ORIGINAL SOURCE:
              (A) ORGANISM: rat
              (F) TISSUE TYPE: skeletal muscle myoblast
              (H) CELL LINE: L6

(xi) SEQUENCE DESCRIPTION: SEQ ID NO:7:

Val Glu Gln Asp Tyr
1               5

(2) INFORMATION FOR SEQ ID NO:8:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:8:

GTAATACGAC TCACTATAGG GGAGAGCT                                              28

(2) INFORMATION FOR SEQ ID NO:9:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:9:

CTCCCCTATA GTGAGTCGTA TTACTGCA                                              28

(2) INFORMATION FOR SEQ ID NO:10:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: DNA (synthetic)

(xi) SEQUENCE DESCRIPTION: SEQ ID NO:10:

CTAGTCTATA GTGTCACCTA AATCGTGGGT AC                                         32

(2) INFORMATION FOR SEQ ID NO:11:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:11:

CACGATTTAG GTGACACTAT AGA                                    23

(2) INFORMATION FOR SEQ ID NO:12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

AATATAGTCG ACCACCATGG AGAACCCCTA CGTTGGGCGA GCGA              44

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

CGGCGGACTA GTTCAGACCT GCACGGGCAG TGTCTGG                      37

(2) INFORMATION FOR SEQ ID NO:14:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

GCCGCCACTA GTTCAGTGGT GGTGGTGGTG GTGGACCTGC ACGGGCAGTG TCTGG  55

(2) INFORMATION FOR SEQ ID NO:15:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

CGGCGGACTA GTTCATGAGC CTCTTTCACT CGTGGTCTCA AACT              44

(2) INFORMATION FOR SEQ ID NO:16:

(i) SEQUENCE CHARACTERISTICS:
        (A) LENGTH: 62 base pairs
        (B) TYPE: nucleic acid
        (C) STRANDEDNESS: single

```
        (D) TOPOLOGY: linear (ii) MOLECULE TYPE: DNA (synthetic)

(xi) SEQUENCE DESCRIPTION: SEQ ID NO:16:

GCCGCCACTA GTTCAGTGGT GGTGGTGGTG GTGTGAGCCT CTTTCACTCG TGGTCTCAAA       60

CT                                                                     62
```